(12) United States Patent
Li et al.

(10) Patent No.: US 9,034,886 B2
(45) Date of Patent: May 19, 2015

(54) 4-AMINOQUINAZOLINE DERIVATIVES AND USES THEREOF

(75) Inventors: Jianqi Li, Shanghai (CN); Qingwei Zhang, Shanghai (CN); Wangping Cai, Jiangsu (CN)

(73) Assignees: Shanghai Institute of Pharmaceutical Industry, Shanghai (CN); Jiangsu Hengyi Pharmaceutical Co., Ltd., Nanjing, Jiangsu Province (CN)

( * ) Notice: Subject to any disclaimer, the term of this patent is extended or adjusted under 35 U.S.C. 154(b) by 0 days.

(21) Appl. No.: 14/124,402

(22) PCT Filed: May 10, 2012

(86) PCT No.: PCT/CN2012/075297
§ 371 (c)(1),
(2), (4) Date: Dec. 6, 2013

(87) PCT Pub. No.: WO2012/155806
PCT Pub. Date: Nov. 22, 2012

(65) Prior Publication Data
US 2014/0235633 A1    Aug. 21, 2014

(30) Foreign Application Priority Data
May 13, 2011  (CN) .......................... 2011 1 0124632

(51) Int. Cl.
| | | |
|---|---|---|
| *A01N 43/54* | (2006.01) | |
| *A61K 31/517* | (2006.01) | |
| *C07D 401/00* | (2006.01) | |
| *C07D 239/94* | (2006.01) | |
| *C07D 401/12* | (2006.01) | |
| *C07D 405/04* | (2006.01) | |
| *C07D 405/12* | (2006.01) | |
| *C07D 409/12* | (2006.01) | |

(52) U.S. Cl.
CPC ............ *C07D 239/94* (2013.01); *C07D 401/12* (2013.01); *C07D 405/04* (2013.01); *C07D 405/12* (2013.01); *C07D 409/12* (2013.01)

(58) Field of Classification Search
CPC ..... C07D 239/72; C07D 401/00; A01N 43/54
USPC ................................ 514/266.2; 544/283, 284
See application file for complete search history.

(56) References Cited

FOREIGN PATENT DOCUMENTS

| WO | 03024448 | | 3/2003 | | |
|---|---|---|---|---|---|
| WO | WO03024448 | * | 3/2003 | ........... | C07D 401/00 |
| WO | 2008113255 | | 9/2008 | | |
| WO | WO 2008113255 | * | 9/2008 | ........... | C07D 401/00 |

OTHER PUBLICATIONS

International Search Report for PCT/CN2012/075297 dated Jul. 16, 2012.
Grignani et al., "Fusion proteins of the retinoic acid receptor-alpha recruit histone deacetylase in promyelocytic leukaemia", Nature, Feb. 19, 1998, 391:815.
Grunstein, "Histone acetylation in chromatin structure and transcription", Nature, Sep. 25, 1997, 389:349.
Lin et al,. "Role of the histone deacetylase complex in acute promyelocytic leukaemia", Nature, Feb. 19, 1998, 391:811.
Marks et al., "Histone deacetylases and cancer: Causes and therapies", Nature, Dec. 2001, 1:194.
Ruijter et al., Histone deacetylases (HDACs): Characterization of the classical HDAC family, Biochem. J., 2003, 370:737-749.

* cited by examiner

*Primary Examiner* — Paul V. Ward
(74) *Attorney, Agent, or Firm* — Andrus Intellectual Property Law, LLP

(57) ABSTRACT

The present invention provides a 4-aminoquinazoline derivative having the chemical structure of the following formula, and the use thereof. It is demonstrated by the pharmacological experiment that, the compound or a salt thereof according to the present invention not only has distinct inhibitory effect on histone deacetylases, but also has stronger differentiation induction and anti-proliferative activities for certain tumor cells. It can be used in the treatment of cancers and diseases related to cell differentiation and proliferation. Excellent efficacy is observed especially for leukemia and a solid tumor. As demonstrated by the animal test, the compound or a salt thereof according to the present invention is less toxic.

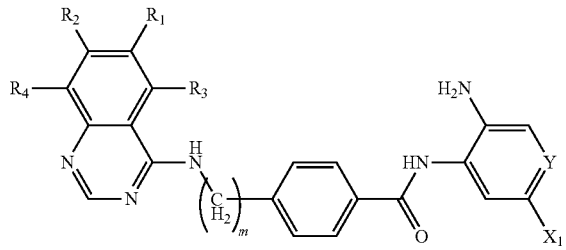

2 Claims, No Drawings

4-AMINOQUINAZOLINE DERIVATIVES AND USES THEREOF

CROSS REFERENCE TO RELATED APPLICATION

The present application is the U.S. national stage of International Application PCT/CN2012/075297, filed May 10, 2012, which international application was published on Nov. 22, 2012, as International Publication No. WO20121155806. The International Application claims priority to Chinese Patent Application No. 201110124632.5, filed May 13, 2011, the contents of which are incorporated herein by reference in their entireties.

TECHNICAL FIELD

The present invention relates to a method for synthesizing 4-aminoquinazoline derivatives capable of inhibiting histone deacetylases, and the use thereof for treating malignant tumors and diseases related to cell differentiation and proliferation.

BACKGROUND

Acetylation and deacetylation of histones in the chromatin is a key step in regulating the gene expression, whereas abnormality in gene expression constitutes the molecular biological basis for the occurrence of tumors and some hereditary and metabolic diseases. The acetylation degree of histones is co-regulated by histone acetylases (HATs) and histone deacetylases (HDACs). Overexpression of HDACs and the recruitment thereof by transcription factors would cause abnormal inhibition of specific genes, leading to tumors and other diseases (Grunstein, M., 1997, Nature, 389:349-352). The HDAC activity is reported to be related to the occurrence of cancers, immunological diseases, and some mental and cardiovascular diseases (Ruijter, A-J-M., 2003, Biochem. J., 370:737-749; Grignani, F., 1998, Nature, 391:815-818; Lin, R-J, 1998, 391:811-814; Marks, P-A., 2001, Nature Reviews Cancer, 1:194).

It is experimentally demonstrated that the inhibitor of HDACs can increase the level of acetylation of histones in the chromatin, accordingly causing the activation and expression of specific genes and in turn the terminal differentiation of cells or the apoptosis of cancer cells. Preliminary clinical research has shown that it is safe for a human to achieve a high acetylation level of histones by inhibiting the HDAC activity. Therefore, HDACs are of the newest and hottest targets in the current research and development area for chemotherapeutic drugs.

HDAC is an enzyme superfamily with its members known to occur in four classes comprising 18 different subtypes, wherein Class I comprises four subtypes, namely HDAC1, 2, 3, and 8; Class II comprises six subtypes, namely HDAC4, 5, 6, 7, 9, and 10 (wherein HDAC4, 5, 7, and 9 belong to Class IIa, and HDAC6 and 10 belong to Class IIb); Class IV only comprises one subtype, HDAC11 which shares certain homology with the previous two classes; Class III comprises seven subtypes in total including Sirt1-7 which do not share any structural homology with the previous three classes. At present, HDAC subtypes in Class I and Class II are relatively better studied, but not much is known about Class III and Class IV of HDACs. HDAC Class I proteins mainly localize in the nucleus and are expressed in cells of multiple tissues. HDAC Class II proteins mainly localize in the cytoplasm (or shuttle between the nucleus and the cytoplasm) and are only expressed in cells of some kinds of tissues. Results from research using small interfering RNA technique and animal gene knockout technique have shown comprehensively that some HDAC subtypes from Class I and Class IIa could be the target relevant to an antitumor effect, wherein inhibiting HDAC1, 2 and 3 can result in inhibition of cell proliferation; inhibiting HDAC4 can affect the repair processes of DNA damage; and inhibiting HDAC7 can induce apoptosis of thymocytes.

Research in recent years has fully demonstrated that the overexpression or abnormal activities of HDACs play an important role in the occurrence and development of leukemia and a solid tumor. It is shown that significant in vivo and in vitro antitumor effects can be achieved by inhibiting the HDAC functional activity. HDAC inhibitors currently under investigation in clinical trials can be categorized into four groups based on their chemical structures, namely:

(1) hydroxamic acids, e.g. trichostatin (TSA), and suberolanilide hydroxamic acid (SAHA);
(2) cyclic tetrapeptides, e.g. Apicidin;
(3) short-chain or aromatic fatty acids, e.g. sodium butyrate; and
(4) benzamides, e.g. MS-275.

The first two groups of compounds are non-selective HDAC inhibitors and inhibit all HDAC subtypes in Class I and Class II. Short-chain or aromatic fatty acids generally have weaker inhibition activities and need to be tested in combination with other medicaments to provide stronger effects. Benzamides, however, are selective with targeting effects and mainly inhibit Class I HDACs (including HDAC subtypes 1, 2 and 3 but not HDAC8) and part of Class IIa HDACs and have no inhibitory effect on Class IIb HDACs. At present, antitumor drugs targeting HDACs are being investigated worldwide. SAHA (Trade name Zolinza) developed by Merk Company has been approved by FDA for treating cutaneous T-cell lymphoma (CTCL) and launched at the end of 2006. This not only indicates the end of the confirmatory research phase for the concept of using HDAC as a novel drug target, but also implies a broad prospect of developing HDAC inhibitors as novel antitumor drugs. Meanwhile, studies on the mechanisms underlying the antitumor effect of HDAC inhibitors are gradually going deeper and encompass multiple aspects related to the tumor formation and development such as induction of tumor cell apoptosis, inhibition of tumor cell cycle, induction of tumor cell differentiation, inhibition of angiogenesis, inhibition of tumor metastasis, and regulation of the immune system function etc.

Due to the structure similarity of the HDAC subtypes, most of the present HDAC inhibitors are not selective towards these subtypes and typically inhibit multiple subtypes at the same time, causing certain side effects and thus affecting the druggability of the inhibitors. Consequently, research focus and technical difficulty in the prior art of this area is to obtain a novel and effective anti-malignant tumor agent with low adverse side effects and high safety by designing and synthesizing highly selective HDAC inhibitors, especially the benzamides.

SUMMARY OF THE INVENTION

One of the technical problems to be solved by the present invention is to disclose a class of 4-aminoquinazoline derivatives to meet the need in the clinical application;

Another technical problem to be solved by the present invention is to disclose the use of the 4-aminoquinazoline derivatives in the preparation of a medicament for treating malignant tumors and diseases related to cell differentiation and proliferation.

The 4-aminoquinazoline derivative in accordance with the present invention is a compound having the chemical structure of the following formula or a salt thereof:

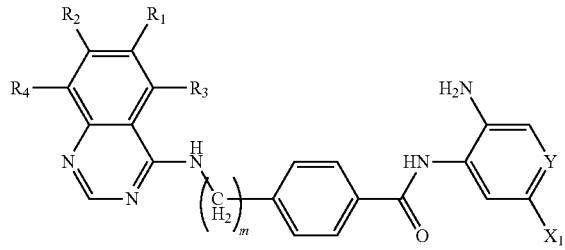

wherein $R_1$, $R_2$, $R_3$ and $R_4$ each independently represent hydrogen, halogen, amino, nitro, hydroxyamino, carboxyl, $C_1$-$C_4$ alkoxycarbonyl, $C_1$-$C_4$ aminoalkyl, $C_1$-$C_4$ aminoalkyl, $C_1$-$C_4$ alkylamino, $C_1$-$C_4$ alkyl, $C_1$-$C_4$ amido, (E)-4-(dimethylamino)-2-butanamido, alkoxy, guanidyl, carbamido, trifluoromethyl, $C_1$-$C_4$ sulfonyl, aryl sulfonyl, substituted phenyl, phenyl, heterocyclyl or substituted heterocyclyl;

Y is N or C;

$X_1$ is hydrogen, halogen, substituted phenyl, phenyl, heterocyclyl or substituted heterocyclyl;

m=0 or 1;

when $R_3$, $R_4$ and $R_5$ are all hydrogen, then Y is C, and m=1;

when $X_1$ is hydrogen or F, Y is C, and m=1, then $R_1$ and $R_2$ are not both methoxy;

the substituent on the substituted phenyl or substituted heterocyclyl is halogen, amino, hydroxy, nitro, cyano, $C_1$-$C_4$ alkyl, $C_1$-$C_4$ alkoxy, $C_1$-$C_4$ aminoalkyl, $C_1$-$C_4$ alkylamino, $C_1$-$C_4$ sulfonyl, $C_2$-$C_4$ acyl, $C_2$-$C_4$ amido, $C_1$-$C_4$ thioalkyl, trifluoromethyl, $C_1$-$C_4$ carboxyl, $C_1$-$C_4$ alkoxycarbonyl, phenyl or heterocyclyl;

the substituted phenyl is a benzene ring with 1 to 4 substituents, wherein the substituent is halogen, hydroxy, nitro, cyano, alkoxy, $C_1$-$C_4$ alkyl or amino group;

the heterocyclyl is a saturated or unsaturated five- or six-membered ring containing one or more hetero atoms selected from the group consisting of N, O and S;

the halogen is F, Cl, Br or I;

preferably, the $C_1$-$C_4$ alkyl represented by $R_1$, $R_2$, $R_3$ and $R_4$ refers to a saturated hydrocarbon chain that is branched, unbranched, or cyclic and contains the specified number of carbon atoms, preferably methyl, ethyl, propyl, isopropyl, cyclopropyl, butyl, isobutyl, sec-butyl, tert-butyl or cyclobutyl;

preferably, the alkoxy represented by $R_1$, $R_2$, $R_3$ and $R_4$ is $C_1$-$C_4$ alkoxy, substituted benzyloxy, pyrrolidin-1-yl-($C_2$-$C_4$) alkoxy, morpholin-1-yl-($C_2$-$C_4$)alkoxy, piperazin-1-yl-($C_2$-$C_4$)alkoxy, N-methyl piperazin-1-yl-($C_2$-$C_4$)alkoxy or piperidin-1-yl-($C_2$-$C_4$)alkoxy;

said amino means —$NH_2$;

preferably, the $C_1$-$C_4$ aminoalkyl represented by $R_1$, $R_2$, $R_3$ and $R_4$ is preferably aminoethyl, 1-aminopropyl or 2-aminopropyl;

preferably, the $C_1$-$C_4$ alkylamino represented by $R_1$, $R_2$, $R_3$ and $R_4$ is preferably N-methylamino, N-ethylamino or N-isopropylamino;

said amido refers to —C(O)NH—, wherein "$C_1$-$C_4$ amido" is a "$C_1$-$C_4$ alkyl" linked to an "amido", preferably acetamido ($CH_3C(O)NH$—), propionamido ($CH_3CH_2C(O)NH$—), butanamido or isobutanamido;

said sulfonyl refers to —$SO_2$—; wherein "$C_1$-$C_4$ sulfonyl" means a "$C_1$-$C_4$ alkyl" linked to a "sulfonyl", preferably methylsulfonyl, ethylsulfonyl, propylsulfonyl, isopropylsulfonyl, n-butylsulfonyl, isobutylsulfonyl, or sec-butylsulfonyl;

said salt is a hydrochloride, hydrobromide, sulfate, acetate, lactate, tartrate, tannate, citrate, trifluoroacetate, malate, maleate, succinate, tosylate or mesylate;

said salt contains no crystal water, or one or more molecules of crystal water, preferably 0.5-3.0 molecules of crystal water.

Preferable compounds comprise:

V-1 N-(2-aminophenyl)-4-(quinazoline-4-amino)benzamide,

V-2 N-(2-amino-4-pyridyl)-4-(quinazoline-4-amino)benzamide,

V-3 N-(2-amino-5-fluorophenyl)-4-(quinazoline-4-amino)benzamide,

V-4 N-(2-amino-4-pyridyl)-4-(6,7-dimethoxyquinazoline-4-amino)benzamide,

V-5 N-(2-aminophenyl)-4-(6-methoxyquinazoline-4-amino)benzamide,

V-6 N-(2-amino-5-fluorophenyl)-4-(6-methoxyquinazoline-4-amino)benzamide,

V-7 N-(2-aminophenyl)-4-(5-methoxyquinazoline-4-amino)benzamide,

V-8 N-(2-amino-4-pyridyl)-4-(5-methoxyquinazoline-4-amino)benzamide,

V-9 N-(2-aminophenyl)-4-(8-methoxyquinazoline-4-amino)benzamide,

V-10 N-(2-amino-5-fluorophenyl)-4-(8-methoxyquinazoline-4-amino)benzamide,

V-11 N-(2-aminophenyl)-4-(6-nitroquinazoline-4-amino)benzamide,

V-12 N-(2-aminophenyl)-4-(6-fluoroquinazoline-4-amino)benzamide,

V-13 N-(2-aminophenyl)-4-(7-fluoroquinazoline-4-amino)benzamide,

V-14 N-(2-amino-5-fluorophenyl)-4-(8-fluoroquinazoline-4-amino)benzamide,

V-15 N-(2-aminophenyl)-4-(6,7-dimethoxyethoxyquinazoline-4-amino)benzamide,

V-16 N-(2-amino-4-pyridyl)-4-(6,7-dimethoxyethoxyquinazoline-4-amino)benzamide,

V-17 N-(2-aminophenyl)-4-[7-methoxy-6-(3-morpholinylpropoxy)quinazoline-4-amino]benzamide, V-18 N-(2-amino-5-fluorophenyl)-4-[7-methoxy-6-(3-morpholinyl propoxy)quinazoline-4-amino]benzamide, V-19 N-(2-aminophenyl)-4-[6-(5-((2-(methylsulfonyl)ethylamino)methyl)furyl)quinazoline-4-amino]benzamide, V-20 N-(2-amino-5-fluorophenyl)-4-[6-(5-((2-(methylsulfonyl)ethyl amino)methyl)furyl)quinazoline-4-amino]benzamide, V-21 N-(2-aminophenyl)-4-(6-acetamidoquinazoline-4-amino)benzamide.

V-22 N-(2-aminophenyl)-4-(6-methoxycarbonylmethyl quinazoline-4-amino)benzamide, V-23 N-[2-amino-5-(2-thienyl)phenyl]-4-(6,7-dimethoxyquinazoline-4-amino)benzamide, V-24 N-[2-amino-5-(phenyl)phenyl]-4-(6,7-dimethoxyquinazoline-4-amino)benzamide, V-25 NV-[2-amino-5-(2-furyl)phenyl]-4-(6,7-dimethoxyquinazoline-amino)benzamide, V-26 N-(2-amino-4-pyridyl)-4-[(quinazoline-4-amino)methyl]benzamide, V-27 N-(2-aminophenyl)-4-[(quinazoline-4-amino)methyl]benzamide,
V-28 N-[2-amino-5-(2-thienyl)phenyl]-4-[(quinazoline-4-amino)methyl]benzamide,
V-29 N-(2-amino-5-fluorophenyl)-4-[(quinazoline-4-amino)methyl]benzamide,
V-30 N-(2-amino-4-pyridyl)-4-[(6,7-dimethoxyquinazoline-4-amino)methyl]benzamide,
V-31 N-[2-amino-5-(2-thienyl)phenyl]-4-[(6,7-dimethoxyquinazoline-4-amino)methyl]benzamide,
V-32 N-(2-aminophenyl)-4-[(7-methoxyquinazoline-4-amino)methyl]benzamide,
V-33 N-(2-aminophenyl)-4-[(6-methoxyquinazoline-4-amino)methyl]benzamide,
V-34 N-(2-aminophenyl)-4-[(8-methoxyquinazoline-4-amino)methyl]benzamide,
V-35 N-(2-amino-5-fluorophenyl)-4-[(8-methoxyquinazoline-4-amino)methyl]benzamide,
V-36 N-(2-amino-5-(phenyl)phenyl)-4-[(8-methoxyquinazoline-4-amino)methyl]benzamide,
V-37 N-(2-aminophenyl)-4-[(6-nitroquinazoline-4-amino)methyl]benzamide,
V-38 N-(2-aminophenyl)-4-[(6,7-dimethoxyethoxyquinazoline-4-amino)methyl]benzamide,
V-39 N-(2-amino-4-pyridyl)-4-[(6,7-dimethoxyethoxyquinazoline-4-amino)methyl]benzamide,
V-40 N-(2-amino-5-fluorophenyl)-4-[(6,7-dimethoxyethoxyquinazoline-4-amino)methyl]benzamide,
V-41 N-(2-aminophenyl)-4-[(7-methoxy-6-(3-morpholinylpropoxy)quinazoline-4-amino)methyl]benzamide,
V-42 N-(2-amino-4-pyridyl)-4-[(7-methoxy-6-(3-morpholinylpropoxy)quinazoline-4-amino)methyl]benzamide,
V-43 N-(2-aminophenyl)-4-[(8-fluoroquinazoline-4-amino)methyl]benzamide,
V-44 N-(2-amino-4-pyridyl)-4-[(8-fluoroquinazoline-4-amino)methyl]benzamide,
V-45 N-(2-amino-5-(2-furyl)phenyl)-4-[(8-fluoroquinazoline-4-amino)methyl)]benzamide,
V-46 N-(2-aminophenyl)-4-[(6-acetamidoquinazoline-4-amino)methyl]benzamide,
V-47 N-(2-amino-4-pyridyl)-4-[(6-acetamidoquinazoline-4-amino)methyl]benzamide, or
V-48 N-[2-amino-5-(2-furyl)phenyl]-4-[(6-acetamidoquinazoline-4-amino)methyl]benzamide.

Their structures are as follows:

TABLE 1

Structures of the prefered compounds

| Serial number | Structure |
| --- | --- |
| V-1 | 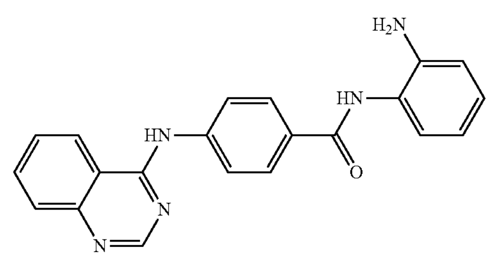 [SMILES: Nc1ccccc1NC(=O)c1ccc(Nc2ncnc3ccccc23)cc1] |
| V-2 | 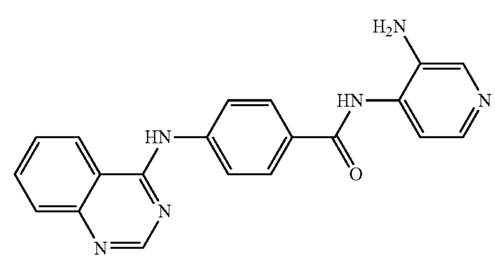 [SMILES: Nc1cnccc1NC(=O)c1ccc(Nc2ncnc3ccccc23)cc1] |
| V-3 | 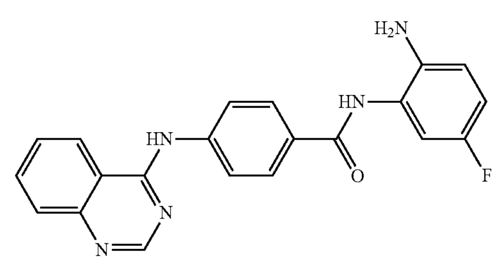 [SMILES: Nc1ccc(F)cc1NC(=O)c1ccc(Nc2ncnc3ccccc23)cc1] |

TABLE 1-continued

Structures of the prefered compounds

| Serial number | Structure |
|---|---|
| V-4 | 6,7-dimethoxyquinazolin-4-yl-NH-C6H4-C(O)NH-(3-aminopyridin-4-yl) |
| V-5 | 6-methoxyquinazolin-4-yl-NH-C6H4-C(O)NH-(2-aminophenyl) |
| V-6 | 6-methoxyquinazolin-4-yl-NH-C6H4-C(O)NH-(2-amino-5-fluorophenyl) |
| V-7 | 5-methoxyquinazolin-4-yl-NH-C6H4-C(O)NH-(2-aminophenyl) |
| V-8 | 5-methoxyquinazolin-4-yl-NH-C6H4-C(O)NH-(3-aminopyridin-4-yl) |
| V-9 | 8-methoxyquinazolin-4-yl-NH-C6H4-C(O)NH-(2-aminophenyl) |

TABLE 1-continued

Structures of the prefered compounds

| Serial number | Structure |
|---|---|
| V-10 | 4-((8-methoxyquinazolin-4-yl)amino)-N-(2-amino-5-fluorophenyl)benzamide |
| V-11 | 4-((6-nitroquinazolin-4-yl)amino)-N-(2-aminophenyl)benzamide |
| V-12 | 4-((6-fluoroquinazolin-4-yl)amino)-N-(2-aminophenyl)benzamide |
| V-13 | 4-((7-fluoroquinazolin-4-yl)amino)-N-(2-aminophenyl)benzamide |
| V-14 | 4-((8-fluoroquinazolin-4-yl)amino)-N-(2-amino-5-fluorophenyl)benzamide |
| V-15 | 4-((6,7-bis(2-methoxyethoxy)quinazolin-4-yl)amino)-N-(2-aminophenyl)benzamide |

TABLE 1-continued
Structures of the prefered compounds
| Serial number | Structure |
|---|---|
| V-16 | 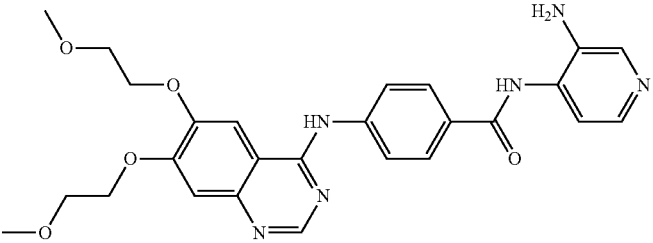 [SMILES: COCCOc1cc2ncnc(Nc3ccc(C(=O)Nc4ccncc4N)cc3)c2cc1OCCOC] |
| V-17 | 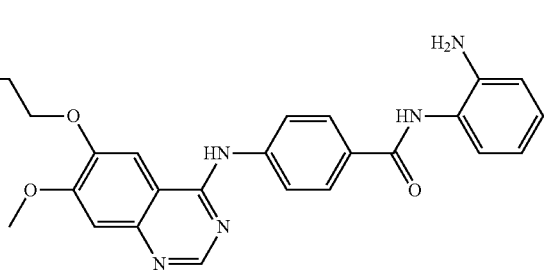 |
| V-18 | 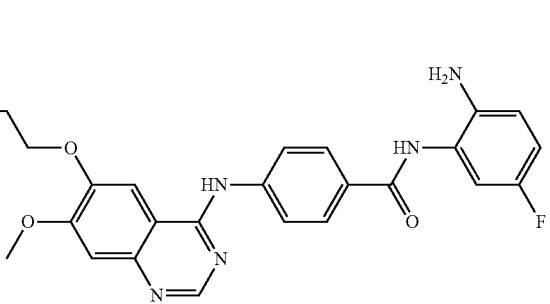 |
| V-19 | 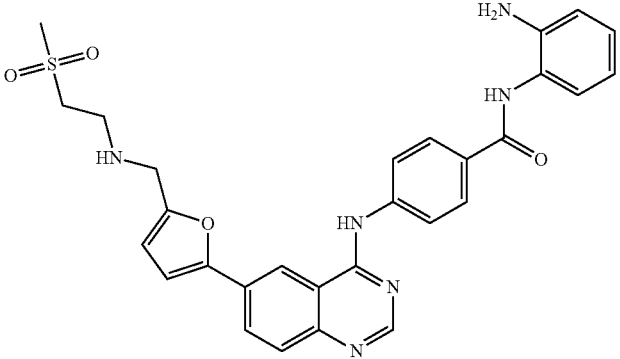 [SMILES: CS(=O)(=O)CCNCc1ccc(-c2ccc3ncnc(Nc4ccc(C(=O)Nc5ccccc5N)cc4)c3c2)o1] |

TABLE 1-continued

Structures of the prefered compounds

| Serial number | Structure |
|---|---|
| V-20 | 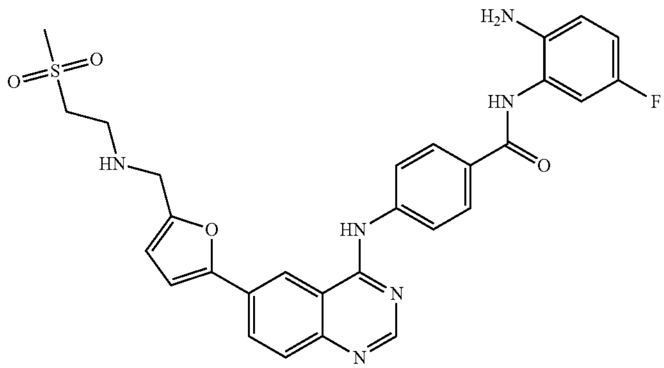 [SMILES: CS(=O)(=O)CCNCc1ccc(-c2ccc3ncnc(Nc4ccc(C(=O)Nc5cc(F)ccc5N)cc4)c3c2)o1] |
| V-21 | 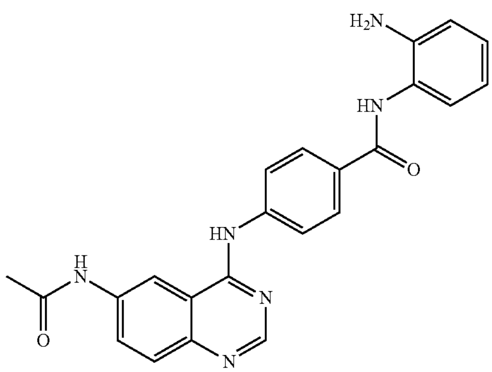 [SMILES: CC(=O)Nc1ccc2ncnc(Nc3ccc(C(=O)Nc4ccccc4N)cc3)c2c1] |
| V-22 | 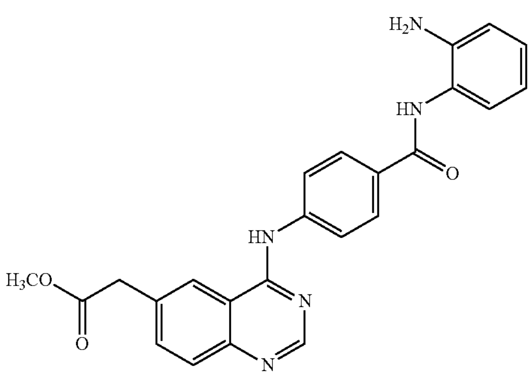 [SMILES: COC(=O)Cc1ccc2ncnc(Nc3ccc(C(=O)Nc4ccccc4N)cc3)c2c1] |
| V-23 | 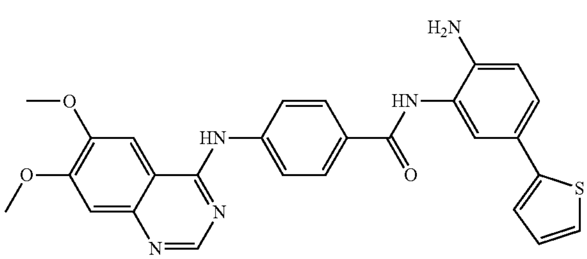 |

TABLE 1-continued
Structures of the prefered compounds
| Serial number | Structure |
|---|---|
| V-24 | 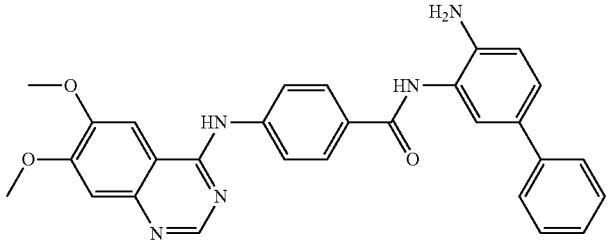 [SMILES: COc1cc2ncnc(Nc3ccc(C(=O)Nc4cc(-c5ccccc5)ccc4N)cc3)c2cc1OC] |
| V-25 | 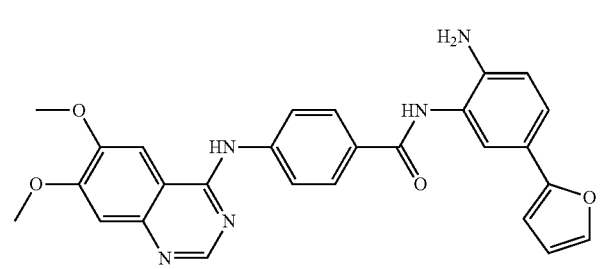 |
| V-26 | 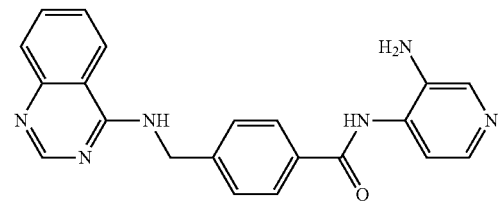 [SMILES: Nc1cnccc1NC(=O)c1ccc(CNc2ncnc3ccccc23)cc1] |
| V-27 | 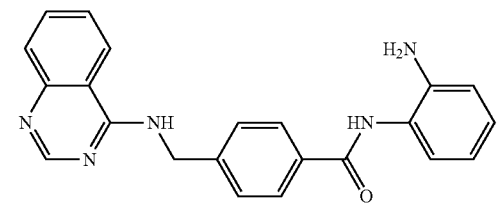 [SMILES: Nc1ccccc1NC(=O)c1ccc(CNc2ncnc3ccccc23)cc1] |
| V-28 | 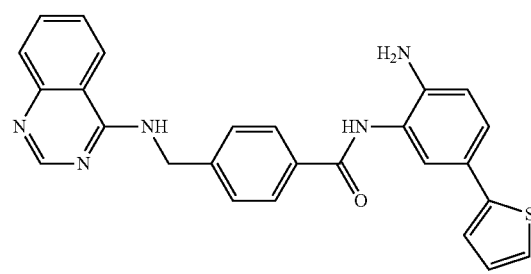 [SMILES: Nc1ccc(-c2cccs2)cc1NC(=O)c1ccc(CNc2ncnc3ccccc23)cc1] |
| V-29 | 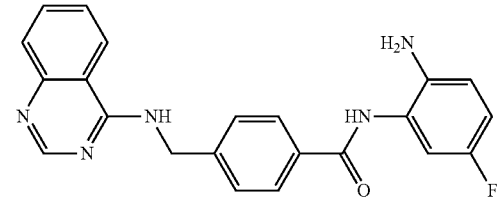 |

TABLE 1-continued

Structures of the prefered compounds

| Serial number | Structure |
|---|---|
| V-30 | 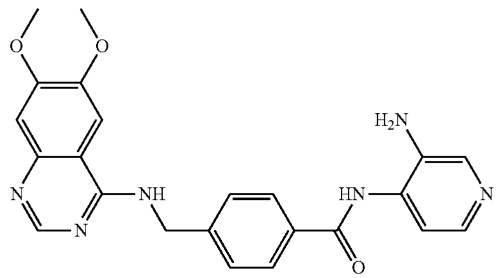 [SMILES: COc1cc2ncnc(NCc3ccc(C(=O)Nc4ccncc4N)cc3)c2cc1OC] |
| V-31 | 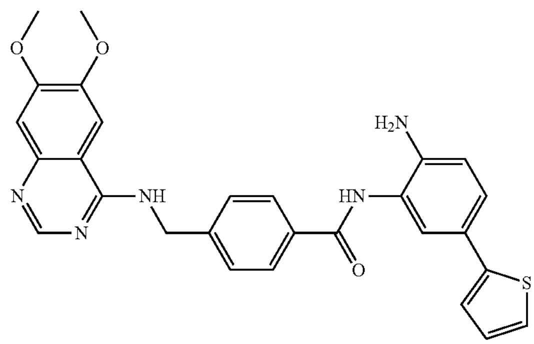 [SMILES: COc1cc2ncnc(NCc3ccc(C(=O)Nc4cc(-c5cccs5)ccc4N)cc3)c2cc1OC] |
| V-32 | 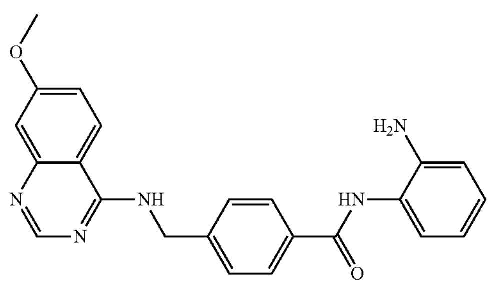 [SMILES: COc1ccc2c(NCc3ccc(C(=O)Nc4ccccc4N)cc3)ncnc2c1] |
| V-33 | 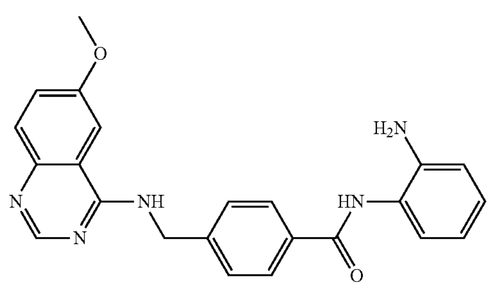 [SMILES: COc1ccc2ncnc(NCc3ccc(C(=O)Nc4ccccc4N)cc3)c2c1] |
| V-34 | 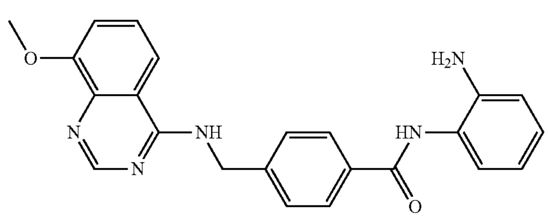 [SMILES: COc1cccc2c(NCc3ccc(C(=O)Nc4ccccc4N)cc3)ncnc12] |

TABLE 1-continued
Structures of the prefered compounds
| Serial number | Structure |
|---|---|
| V-35 | 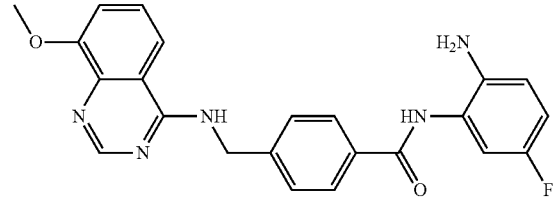 [SMILES: COc1cccc2c(NCc3ccc(C(=O)Nc4cc(F)ccc4N)cc3)ncnc12] |
| V-36 | 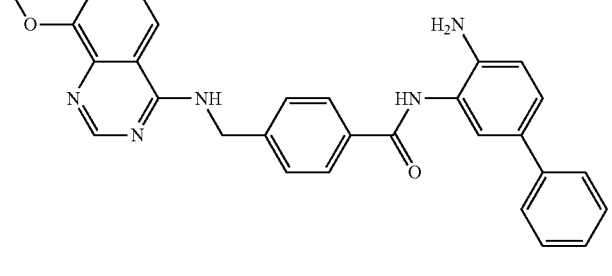 |
| V-37 | 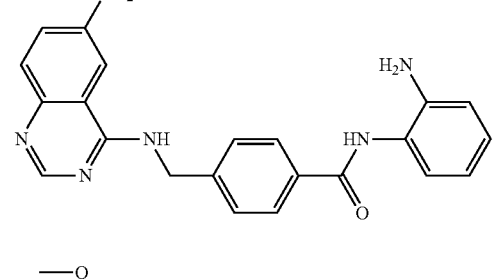 |
| V-38 | 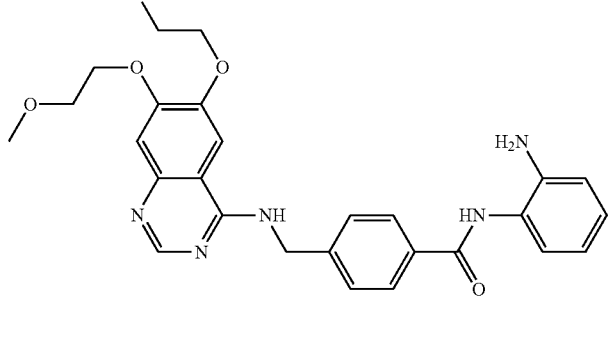 |
| V-39 | 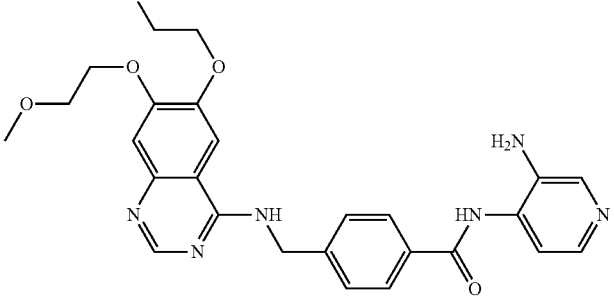 |

TABLE 1-continued

Structures of the prefered compounds

| Serial number | Structure |
|---|---|
| V-40 | 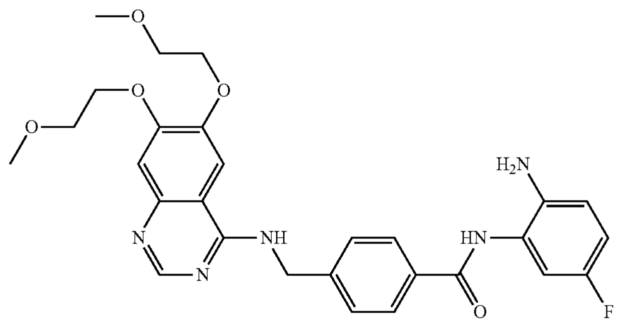 [SMILES: COCCOc1cc2ncnc(NCc3ccc(C(=O)Nc4cc(F)ccc4N)cc3)c2cc1OCCOC] |
| V-41 | 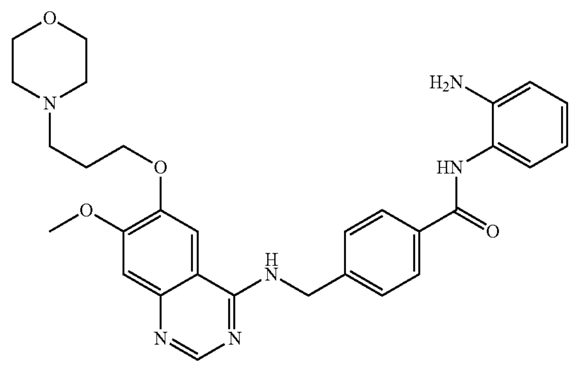 [SMILES: COc1cc2ncnc(NCc3ccc(C(=O)Nc4ccccc4N)cc3)c2cc1OCCCN1CCOCC1] |
| V-42 | 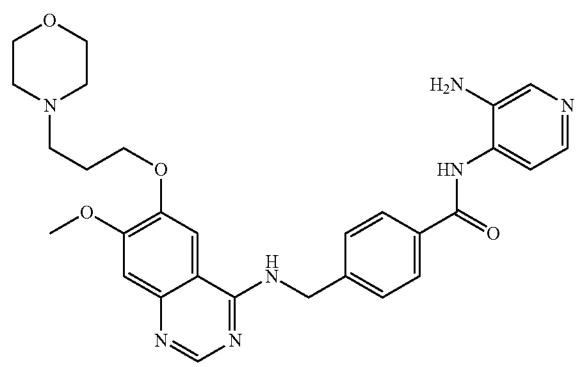 [SMILES: COc1cc2ncnc(NCc3ccc(C(=O)Nc4ccncc4N)cc3)c2cc1OCCCN1CCOCC1] |
| V-43 | 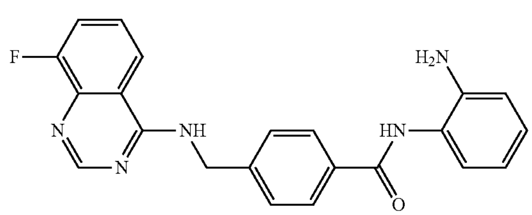 [SMILES: Nc1ccccc1NC(=O)c1ccc(CNc2ncnc3c(F)cccc23)cc1] |
| V-44 | 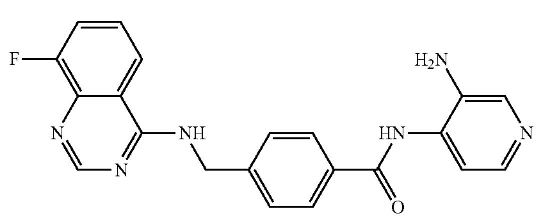 [SMILES: Nc1cnccc1NC(=O)c1ccc(CNc2ncnc3c(F)cccc23)cc1] |

TABLE 1-continued

Structures of the prefered compounds

| Serial number | Structure |
|---|---|
| V-45 | 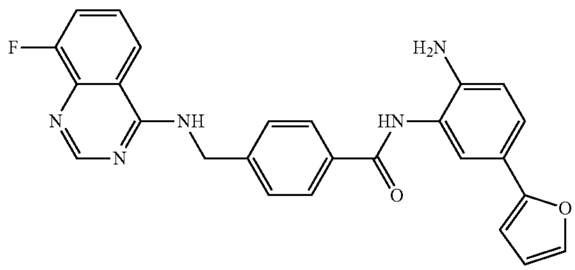 [SMILES: Nc1ccc(-c2ccco2)cc1NC(=O)c1ccc(CNc2ncnc3c(F)cccc23)cc1] |
| V-46 | 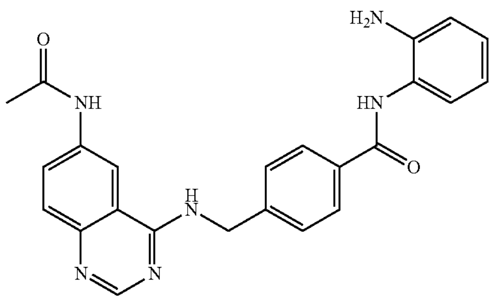 [SMILES: CC(=O)Nc1ccc2ncnc(NCc3ccc(C(=O)Nc4ccccc4N)cc3)c2c1] |
| V-47 | 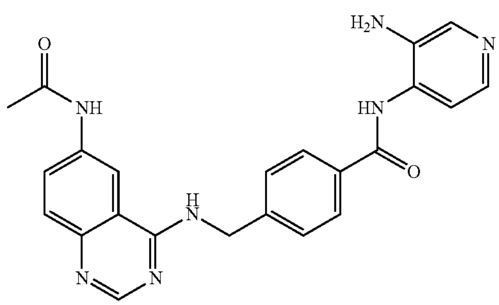 [SMILES: CC(=O)Nc1ccc2ncnc(NCc3ccc(C(=O)Nc4ccncc4N)cc3)c2c1] |
| V-48 | 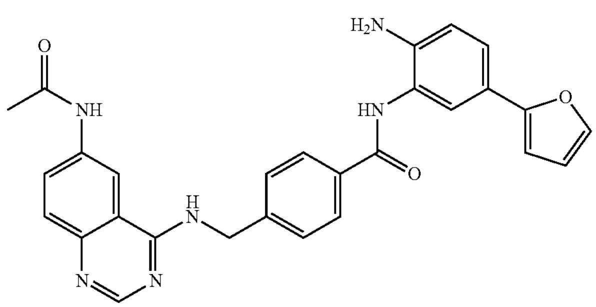 [SMILES: CC(=O)Nc1ccc2ncnc(NCc3ccc(C(=O)Nc4cc(-c5ccco5)ccc4N)cc3)c2c1] |

The compound of the present invention can be synthesized by the following methods:

General Method I:

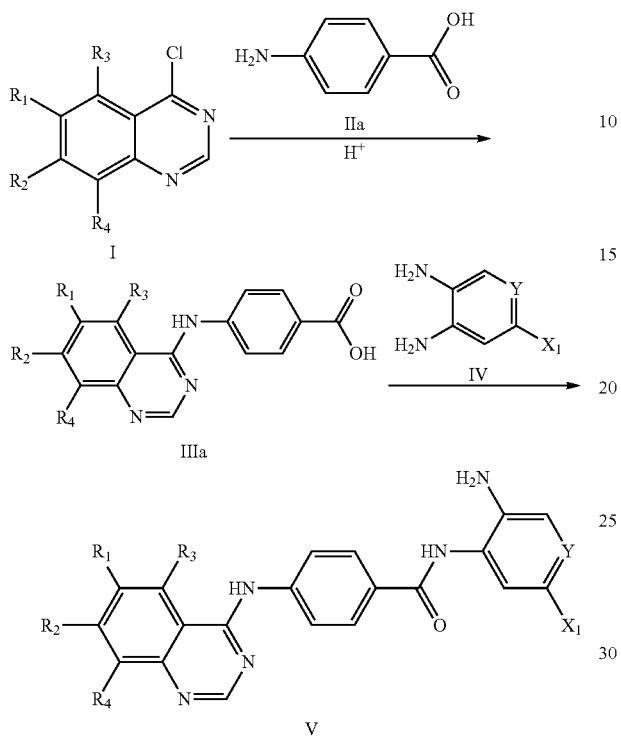

General Method II:

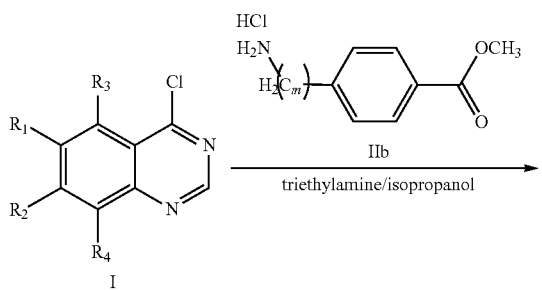

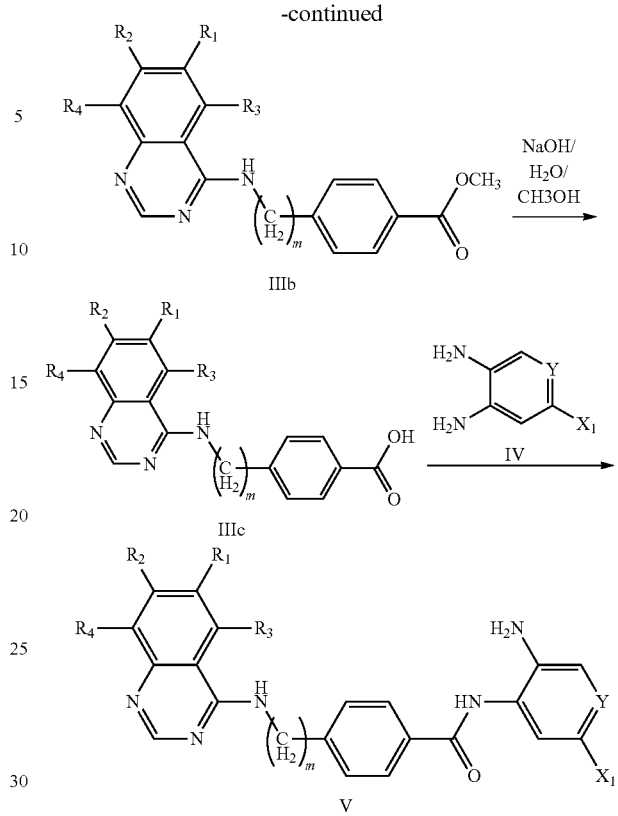

Raw material 1 (10 mmol) and raw material IIa (10 mmol) are dissolved in 50 ml water and 4.2 ml concentrated HCl (12 mol/L), and react under reflux for about 0.1-5 h. The reaction is then stopped and subjected to filtration to provide Intermediate IIIa upon drying.

Intermediate IIIa (1 mmol), Compound IV (1 mmol), and O-(1H-benzotriazol-1-yl)-N,N,N',N'-tetramethylisouronium hexafluorophosphate (HBTU) (0.379 g, 1 mmol) are added sequentially into 10 ml solvent A, and added with triethylamine (2 mmol) dropwise while being kept in an ice bath. The reaction mixture is then stirred at room temperature for 4 h. Subsequently, the reaction mixture is poured into ice water, adjusted with HCl to a pH of about 7-9, and extracted with dichloromethane. The organic phase is dried over anhydrous magnesium sulphate, filtered and concentrated. The residue is purified through column chromatography or recrystallization to provide the target compound V.

General Method II:

Raw material I (10 mmol) and raw material IIb (11 mmol) are dissolved in 30 ml isopropanol and further added with 4 ml triethylamine. The reaction mixture is reacted under reflux for 10 h followed by cooling to room temperature, and then added with a proper amount of water and extracted with ethyl acetate three times. The ethyl acetate layer is collected, dried over anhydrous magnesium sulphate for 3 h and filtered. Intermediate IIIb is obtained after removing the solvent by evaporation.

To Intermediate IIIb (0.01 mol) are added 1.32 g (0.033 mol) sodium hydroxide and then ethanol/water (50 ml/5 ml). The mixture is stirred at 50° C. for 4 h and then concentrated by removing the reaction solvent through evaporation. A proper amount of water is added before filtration. The pH of the filtrate is adjusted with HCl to 4-5. A huge amount of white precipitates are produced, filtered out and dried to provide Intermediate IIIc.

Intermediate IIIc (1 mmol), Compound IV (1 mmol), and O-(1H-benzotriazol-1-yl)-N,N,N',N'-tetramethylisouronium hexafluorophosphate (HBTU) (0.379 g, 1 mmol) are added sequentially into 10 ml solvent A, and added with triethylamine (2 mmol) dropwise while being kept in an ice bath. The reaction mixture is then stirred at room temperature for 4 h. Subsequently, the reaction mixture is poured into ice water, adjusted with HCl to a pH of about 7-9, and extracted with dichloromethane. The organic phase is dried over anhydrous magnesium sulphate, filtered and concentrated. The residue is purified through column chromatography or recrystallization to provide the target compound V.

General Method III (Synthesis of Compound I):

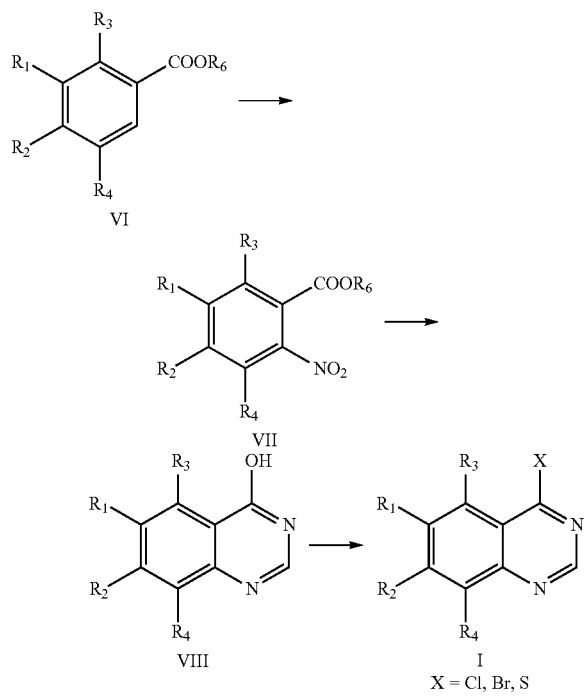

In the General Method III above, $R_6$ is hydrogen, methyl, ethyl or isopropyl.

Compound VI (0.05 mol) are dissolved in 50 ml glacial acetic acid and added with 13 ml, 65-68% by weight of nitric acid dropwise while being stirred in an ice bath. The reaction mixture is then stirred at room temperature for 24 h before poured into 500 ml ice water and extracted with ethyl acetate. The organic phase is combined and washed three times with saturated $NaHCO_3$ aqueous solution, followed by washing with saturated NaCl solution, drying over anhydrous $MgSO_4$, and filtration. The filtrate is concentrated to provide Compound VII. Compound VII (0.10 mol), ammonium formate (63 g, 1.00 mol), 5% Pd—C (5.00 g) and formamide (75 ml) are reacted at 150° C. for 6.5 h. The reaction mixture is cooled to room temperature and a solid is precipitated. The white solid Compound VIII is obtained after filtration. Thionyl chloride (14.9 g) (oxalyl chloride or phosphorus oxychloride) is added dropwise to a solution of Compound VIII (0.15 mol) in N,N-dimethyl formamide (1 ml) and dichloromethane (150 ml) at room temperature while stirring. Upon the addition, the reaction mixture is heated to reflux for 6 h. Cool the reaction mixture to room temperature. Adjust the pH to 7-8 with NaOH aqueous solution. Leave it to separate and take the organic phase to concentrate under reduced pressure. Compound I is thus obtained.

$R_1$, $R_2$, $R_3$, $R_4$, Y, $X_1$ and m in the above General Methods have the same meanings as described before;

In the previous description, solvent A can be: methanol, ethanol, acetonitrile, dichloromethane, N,N-dimethyl formamide, or the like.

Compounds IIa, IIb, IV, VI and HBTU etc. are commercially available.

It is demonstrated by the pharmacological experiment that, the compound or a salt thereof according to the present invention has very strong inhibitory effects on HDACs (Example 49), exhibiting comparative inhibitory activities relative to a similar drug currently being investigated in an abroad clinical trial, MS-275, at concentrations of 2 mM, 200 μM, and 40 μM. Among the compounds, Compounds V-4, V-6, V-14, V-17, V-27, V-33 and V-42 etc. have significantly stronger inhibitory activities than MS-275, and according to the in vitro $IC_{50}$ value against HDACs, Compounds V-4, V-6, V-10, V-11, V-14, V-17. V-27. V-33 and V-42 etc. have better inhibitory activities than MS-275. For example, the $IC_{50}$ value of V-6 against HDACs is 1.83 μM and the $IC_{50}$ value of MS-275 against HDACs is 3.52 μM.

It is demonstrated by the pharmacological experiment that, the compound or a salt thereof according to the present invention shows distinct inhibitory effect on the tumor-associated subtype of HDACs, HDAC1 (Example 50). For example, the inhibitory activities against HDAC1 of Compounds V-7, V-13, V-15, V-16. V-17, V-18. V-19, V-20, V-21, V-24, V-26, and V-27 etc. at both concentrations 10 μM and 1 μM are all superior to that of MS-275, wherein the inhibitory activity against HDAC1 of Compound V-27 shown by its $IC_{50}$=212 nM is significantly stronger than that of MS-275 ($IC_{50}$=668 nM), indicating a stronger targeting capacity towards HDAC subtypes.

It is demonstrated by the pharmacological experiment that, the compound or a salt thereof according to the present invention shows stronger differentiation induction and anti-proliferative effects on multiple strains of tumor cells. Especially, for Hut78 T lymphocytic leukemia cells, Jurkat E6-1 human T-cell lymphoma, PANC-1 human pancreatic cancer cells, A549 human lung cancer cells, K562 human chronic myelogenous leukemia cells, Hep3B2.1-7 human liver cancer cells, MDA-MB-435s human breast cancer cells, Colo320 human colorectal cancer cell lines, and PC-3 human prostate cancer, the anti-proliferative effects are significant (Example 51). Better anti-proliferative effects are observed at both concentrations of 100 μM and 10 μM and the inhibition percentages of Compounds V-9, V-14, V-17, V-19, V-20, V-21. V-24, V-26, and V-27 etc. for multiple strains of tumor cells are superior to that of MS-275. When compared with MS-275, Compound V-27 shows significantly stronger inhibitory effect against tumor cells such as Hut78. K562, and Jurkat E6-1, and stronger inhibitory activity towards Hep3B2.1-7 human liver cancer cells, in which case it has a $IC_{50}$=1.523 μM, significantly better than MS-275 ($IC_{50}$=6.816 μM).

It is demonstrated by the pharmacological experiment that, the compound or a salt thereof according to the present invention is less toxic. The maximum tolerance doses of Compounds V-1, V-4, V-6, V-9, V-13, V-17, V-20, V-25, V-29, V-43, and V-47 when administrated intragastrically are over 5000 mg/kg in mice, and the same of Compounds V-2, V-5, V-1, V-14, V-18, V-22, V-24, V-27 and V-46 are over 2000 mg/kg (Example 52).

It is demonstrated by the pharmacological experiment that, the compound or a salt thereof according to the present invention has smaller cardiotoxicity than another HDAC inhibitor SAHA. For example, the $IC_{50}$ values of Compounds V-9 and V-27 for their effects on hERG potassium current are both above 10 μM, indicating a better cardiac safety (Example 53).

It is demonstrated by the pharmacological experiment that, the compound or a salt thereof according to the present invention provides promising preliminary pharmacokinetic data, showing longer intravenous half-life (1~2 h), higher oral bioavailability (15%~45%), and better druggability (Example 54)

It is demonstrated by the pharmacological experiment conducted in vivo in animals that, the compound or a salt thereof according to the present invention has significant antitumor effect on the nude mice xenograft model (Example 55).

Among the compounds, Compound V-27 shows significant antitumor effect on the nude mice xenograft model A549. At a dose of 50 mg/kg, Compound V-27 can significantly inhibit the growth of tumor, showing an efficacy equivalent to that of the positive control MS-275 at the same dose, but presenting no mortality and significant weight loss in nude mice and indicating lower adverse side effect. MS-275 is a medicament currently being investigated in an abroad phase II clinical trial.

In conclusion, the compound or a salt thereof according to the present invention not only has distinct inhibitory effect on HDACs and the tumor-associated subtype thereof, HDAC1, but also has stronger differentiation induction and anti-proliferative activities for multiple strains of tumor cells. When compared to a similar drug currently being investigated in an abroad clinical trial, MS-275, the compound of the present invention has apparent advantages in its inhibitory activity or antitumor activity, and more than that, it has the following advantages: smaller toxicity, higher cardiac safety, better preliminary pharmacokinetic data, significant antitumor effect on the nude mice xenograft model, comparable efficacy to that of the positive control MS-275, low adverse side effect, and better druggability. The development of the compound or a salt thereof according to the present invention to a medicament for treating cancers and diseases related to cell differentiation and proliferation is novel, inventive and practical, and worth further investigation.

The present invention further relates to a composition comprising a therapeutically effective amount of the compound or a salt thereof according to the present invention and a pharmaceutically acceptable carrier, wherein the carrier can be any substances commonly used as a carrier such as flavors, sweeteners, liquid or solid fillers, diluents or the like, and the composition of the invention can be formulated with a method well-known in this field into a common pharmaceutical formulation such as in the form of tablet, capsule, powder, syrup, liquid, suspension or injection, typically comprising 1-70% by weight and preferably 5-50% by weight of the active ingredient.

Clinically, the compound according to the present invention can be administrated orally or by injection to a mammal (including human), wherein oral administration is mostly preferred. The administration dose can be 0.0001~200 mg/kg body weight per day. The optimal dose varies depending on the individuals, usually starting with a smaller dose and gradually increasing the amount.

The advantage of the present invention is that said compound and the pharmaceutical formulation thereof have a very good efficacy in treating diseases caused by abnormal gene expression such as tumors, endocrine disorders, immune system diseases, genetic diseases and nervous system diseases.

EMBODIMENTS OF THE INVENTION

The present invention will be further illustrated below by reference to the following Examples. It is to be understood that this invention is not limited to the Examples. All percentages present in the present invention are weight percentages, unless otherwise specified.

EXAMPLE 1

V-1 N-(2-aminophenyl)-4-(quinazoline-4-amino) benzamide

Following the General Method I for the preparation of the intermediate IIIa, a white solid (intermediate M-1) of the weight 2.47 g was obtained with 4-chloroquinazoline (1.64 g, 10 mmol) (prepared according to General Method III) and p-aminobenzoic acid (1.37 g, 10 mmol). The yield was 94%.

Following the General Method I for the preparation of the final product V, a white solid of the weight 0.231 g was obtained with M-1 (0.265 g, 1 mmol), o-phenylenediamine (0.108 g, 1 mmol), HBTU (0.379 g, 1 mmol), N,N-dimethylformamide (10 ml), and triethylamine (0.202 g, 2 mmol). The yield was 65.1%.

MS (ESI): [M+H]+=356

1H-NMR (400 MHz, DMSO-d6) δppm: 4.86 (s, 2H), 6.62 (t, 1H, J=6.4 Hz), 6.80 (d, 1H, J=8.0 Hz), 6.98 (t, 1H, J=7.6 Hz), 7.20 (d, 1H, J=8.0 Hz), 7.79-8.11 (m, 7H), 8.49 (dd, 1H, J=2.0 Hz, 6.0 Hz), 8.58 (s, 1H), 9.58 (s, 1H), 9.86 (s, 1H).

EXAMPLE 2

V-2 N-(2-amino-4-pyridyl)-4-(quinazoline-4-amino) benzamide

Following the General Method I for the preparation of the final product V, a white solid of the weight 0.227 g was obtained with M-1 (0.265 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol). The yield was 63.9%.

MS (ESI): [M+H]+=357

1H-NMR (400 MHz, DMSO-d6) δppm: 4.76 (s, 2H), 6.59 (t, 1H, J=6.0 Hz), 6.80 (d, 1H, J=7.6 Hz), 6.98 (m, 1H), 7.16 (d, 1H, J=8.0 Hz), 7.74-8.11 (m, 6H), 8.49 (m, 1H), 8.61 (s, 1H), 9.53 (s, 1H), 9.86 (s, 1H).

EXAMPLE 3

V-3 N-(2-amino-5-fluorophenyl)-4-(quinazoline-4-amino)benzamide

Following the General Method I for the preparation of the final product V, a white solid of the weight 0.19 g was obtained with M-1 (0.265 g, 1 mmol), 4-fluoro-1,2-phenylenediamine (0.126 g, 1 mmol), HBTU (0.379 g, 1 mmol), N,N-dimethylformamide (10 ml), and triethylamine (0.202 g, 2 mmol). The yield was 50.9%.

MS (ESI): [M+H]+=374

1H-NMR (400 MHz, DMSO-d6) δppm: 4.77 (s, 2H), 6.59 (t, 1H, J=6 Hz), 6.80 (d, 1H, J=8.0 Hz), 6.98 (m, 1H), 7.20 (d, 1H, J=8.0 Hz), 7.78-8.14 (m, 6H), 8.49 (m, 1H), 8.69 (s, 1H), 9.58 (s, 1H), 9.89 (s, 1H)

EXAMPLE 4

V-4 N-(2-amino-4-pyridyl)-4-(6,7-dimethoxyquinazoline-4-amino)benzamide

Following the General Method I for the preparation of the intermediate IIIa, a white solid (Intermediate M-4) of the weight 2.44 g was obtained with 6,7-dimethoxy-4-chloroquinazoline (2.24 g, 10 mmol) (prepared according to General Method III) and p-aminobenzoic acid (1.37 g, 10 mmol). The yield was 75%.

Following the General Method I for the preparation of the final product V, a white solid of the weight 0.282 g was obtained with M-4 (0.325 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol). The yield was 67.9%.

MS (ESI): [M+H]+=417
1H-NMR (400 MHz, DMSO-d6) δppm: 3.90 (s, 6H), 5.13 (s, 2H), 7.11 (s, 1H), 7.42 (d, 1H, J=5.2 Hz), 7.49 (d, 2H, J=8.0 Hz), 7.68 (s, 1H), 7.78 (d, 1H, J=5.2 Hz), 7.90 (d, 2H, J=8.0 Hz), 8.08 (s, 1H), 8.31 (s, 1H), 8.54 (t, 1H, J=6.0 Hz), 9.65 (s, 1H).

EXAMPLE 5

V-5 N-(2-aminophenyl)-4-(6-methoxyquinazoline-4-amino)benzamide

Following the General Method I for the preparation of the intermediate IIIa, a white solid (Intermediate M-5) of the weight 2.42 g was obtained with 6-methoxy-4-chloro-quinazoline (1.94 g, 100 mmol) (prepared according to General Method III) and p-aminobenzoic acid (1.37 g, 10 mmol). The yield was 82%.

Following the General Method I for the preparation of the final product V, a white solid of the weight 0.201 g was obtained with M-5 (0.295 g, 1 mmol), o-phenylenediamine (0.108 g, 1 mmol), HBTU (0.379 g, 1 mmol), N,N-dimethylformamide (10 ml), and triethylamine (0.202 g, 2 mmol). The yield was 52.1%.
MS (ESI): [M+H]+=386
1H-NMR (400 MHz, DMSO-d6) δppm: 3.87 (s, 3H), 5.11 (s, 2H), 7.11 (m, 2H), 7.42 (d, 1H, J=5.2 Hz), 7.49 (m, 2H), 7.68 (s, 1H), 7.78 (d, 1H, J=4.8 Hz), 7.90 (d, 2H, J=8.0 Hz), 8.08 (s, 1H), 8.32 (s, 1H), 8.54 (t, 1H, J=6.0 Hz), 9.71 (s, 1H).

EXAMPLE 6

V-6 N-(2-amino-5-fluorophenyl)-4-(6-methoxyquinazoline-4-amino)benzamide

Following the General Method I for the preparation of the final product V, a white solid of the weight 0.276 g was obtained with M-5 (0.295 g, 1 mmol), 4-fluoro-1,2-phenylenediamine (0.126 g, 1 mmol), HBTU (0.379 g, 1 mmol), N,N-dimethylformamide (10 ml), and triethylamine (0.202 g, 2 mmol). The yield was 68.3%.
MS (ESI): [M+H]+=404
1H-NMR (400 MHz, DMSO-d6) δppm: 3.83 (s, 3H), 5.11 (s, 2H), 6.79 (m, 1H), 7.42 (d, 1H, J=5.2 Hz), 7.47 (m, 2H), 7.68 (s, 1H), 7.78 (d, 1H, J=4.8 Hz), 7.90 (d, 2H, J=8.0 Hz), 8.08 (s, 1H), 8.32 (s, 1H), 8.54 (t, 1H, J=6.0 Hz), 9.71 (s, 1H).

EXAMPLE 7

V-7 N-(2-aminophenyl)-4-(5-methoxy-quinazoline-4-amino)benzamide

Following the General Method I for the preparation of the intermediate IIIa, a white solid (Intermediate M-7) of the weight 2.69 g was obtained with 5-methoxy-4-chloro-quinazoline (1.94 g, 10 mmol) (prepared according to General Method III) and p-aminobenzoic acid (1.37 g, 10 mmol). The yield was 91%.

Following the General Method I for the preparation of the final product V, a white solid of the weight 0.191 g was obtained with M-7 (0.295 g, 1 mmol), o-phenylenediamine (0.108 g, 1 mmol), HBTU (0.379 g, 1 mmol), N,N-dimethylformamide (10 ml), and triethylamine (0.202 g, 2 mmol). The yield was 49.6%.
MS (ESI): [M+H]+=386
1H-NMR (400 MHz, DMSO-d6) δppm: 3.81 (s, 3H), 5.34 (s, 2H), 6.88 (m, 2H), 7.35 (m, 1H), 7.49 (m, 2H), 7.68 (s, 1H), 7.78 (d, 1H, J=4.8 Hz), 7.90 (m, 2H), 8.14 (s, 1H), 8.32 (s, 1H), 8.54 (t, 1H, J=6.0 Hz), 9.80 (s, 1H).

EXAMPLE 8

V-8 N-(2-amino-4-pyridyl)-4-(5-methoxy-quinazoline-4-amino)benzamide

Following the General Method I for the preparation of the final product V, a white solid of the weight 0.224 g was obtained with M-7 (0.295 g, 1 mmol), 3,4-diaminopyridine (0.109 g, 1 mmol). HBTU (0.379 g, 1 mmol), N,N-dimethylformamide (10 ml), and triethylamine (0.202 g, 2 mmol). The yield was 57.9%.
MS (ESI): [M+H]+=387
1H-NMR (400 MHz, DMSO-d6) δppm: 3.77 (s, 3H), 5.34 (s, 2H), 6.88 (m, 2H), 7.50 (m, 2H), 7.68 (s, 1H), 7.78 (d, 1H, J=4.8 Hz), 7.90 (m, 2H), 8.14 (s, 1H), 8.32 (s, 1H), 8.54 (t, 1H, J=6.0 Hz), 9.80 (s, 1H)

EXAMPLE 9

V-9 N-(2-aminophenyl)-4-(8-methoxy-quinazoline-4-amino)benzamide

Following the General Method I for the preparation of the intermediate IIIa, a white solid (Intermediate M-9) of the weight 2.51 g was obtained with 8-methoxy-4-chloro-quinazoline (1.94 g, 10 mmol) (prepared according to General Method III) and p-aminobenzoic acid (1.37 g, 10 mmol). The yield was 85%.

Following the General Method I for the preparation of the final product V, a white solid of the weight 0.181 g was obtained with M-9 (0.295 g, 1 mmol), o-phenylenediamine (0.108 g, 1 mmol), HBTU (0.379 g, 1 mmol). N,N-dimethylformamide (10 ml), and triethylamine (0.202 g, 2 mmol). The yield was 47.1%.
MS (ESI): [M+H]+=386
1H-NMR (400 MHz, DMSO-d6) δppm: 3.81 (s, 3H), 5.82 (s, 2H), 6.88 (m, 2H), 7.35 (m, 1H), 7.49 (m, 2H), 7.68 (s, 1H), 7.70 (d, 1H, J=4.8 Hz), 7.90 (m, 2H), 8.11 (s, 1H), 8.32 (s, 1H), 8.50 (t, 1H, J=6.0 Hz), 9.77 (s, 1H).

EXAMPLE 10

V-10 N-(2-amino-5-fluorophenyl)-4-(8-methoxy-quinazoline-4-amino)benzamide

Following the General Method I for the preparation of the final product V, a white solid of the weight 0.182 g was obtained with M-9 (0.295 g, 1 mmol), 4-fluoro-1,2-phenylenediamine (0.126 g, 1 mmol), HBTU (0.379 g, 1 mmol), N,N-dimethylformamide (10 ml), and triethylamine (0.202 g, 2 mmol). The yield was 45.1%.
MS (ESI): [M+H]+=404
1H-NMR (400 MHz, DMSO-d6) δppm: 3.81 (s, 3H), 5.82 (s, 2H), 6.92 (m, 1H), 7.35 (m, 1H), 7.45 (m, 2H), 7.61 (s, 1H), 7.70 (d, 11, J=4.8 Hz), 7.84 (m, 2H), 8.11 (s, 1H), 8.32 (s, 1H), 8.50 (t, 1H, J=6.0 Hz), 9.88 (s, 1H).

EXAMPLE 11

V-11 N-(2-aminophenyl)-4-(6-nitroquinazoline-4-amino)benzamide

Following the General Method I for the preparation of the intermediate IIIa, a pale yellow solid (Intermediate M-11) of the weight 2.79 g was obtained with 6-nitro-4-chloroquinazoline (2.09 g, 10 mmol) (prepared according to General Method III) and p-aminobenzoic acid (1.37 g, 10 mmol). The yield was 90%.

Following the General Method I for the preparation of the final product V, a yellow solid of the weight 0.118 g was obtained with M-11 (0.310 g, 1 mmol), o-phenylenediamine (0.108 g, 1 mmol), HBTU (0.379 g, 1 mmol), N,N-dimethylformamide (10 ml), and triethylamine (0.202 g, 2 mmol). The yield was 29.5%.

MS (ESI): [M+H]+=401

1H-NMR (400 MHz. DMSO-d6) δppm: 5.16 (s, 2H), 7.46 (d, 1H, J=5.2 Hz), 7.81 (d, 1H, J=5.2 Hz), 7.94-8.06 (m, 6H), 8.11 (s, 1H), 8.55 (dd, 1H, J=2.0 Hz, 9.2 Hz), 8.77 (s, 1H), 9.65 (s, 1H), 10.58 (s, 1H).

EXAMPLE 12

V-12 N-(2-aminophenyl)-4-(6-fluoroquinazoline-4-amino)benzamide

Following the General Method I for the preparation of the intermediate IIIa, a white solid (Intermediate M-12) of the weight 2.66 g was obtained with 6-fluoro-4-chloroquinazoline (1.82 g, 10 mmol) (prepared according to General Method III) and p-aminobenzoic acid (1.37 g, 10 mmol). The yield was 94%.

Following the General Method I for the preparation of the final product V, a white solid of the weight 0.192 g was obtained with M-12 (0.283 g, 1 mmol), o-phenylenediamine (0.108 g, 1 mmol), HBTU (0.379 g, 1 mmol), N,N-dimethylformamide (10 ml), and triethylamine (0.202 g, 2 mmol). The yield was 51.3%.

MS (ESI): [M+H]+=374

1H-NMR (400 MHz, DMSO-d6) δppm: 4.88 (s, 2H), 6.62 (t, 1H, J=7.2 Hz), 6.80 (d, 1H, J=8.0 Hz), 6.98 (t, 1H, J=7.6 Hz), 7.20 (d, 1H, J=8.0 Hz), 7.81-8.11 (m, 6H), 8.49 (dd, 1H, J=2.4 Hz, 6.4 Hz), 8.69 (s, 1H), 9.58 (s, 1H), 9.89 (s, 1H).

EXAMPLE 13

V-13 N-(2-aminophenyl)-4-(7-fluoroquinazoline-4-amino)benzamide

Following the General Method I for the preparation of the intermediate IIIa, a white solid (Intermediate M-13) of the weight 2.46 g was obtained with 7-fluoro-4-chloroquinazoline (1.82 g, 10 mmol) (prepared according to General Method III) and p-aminobenzoic acid (1.37 g, 10 mmol). The yield was 87%.

Following the General Method I for the preparation of the final product V, a white solid of the weight 0.176 g was obtained with M-13 (0.283 g, 1 mmol), o-phenylenediamine (0.108 g, 1 mmol), HBTU (0.379 g, 1 mmol), N,N-dimethylformamide (10 ml), and triethylamine (0.202 g, 2 mmol). The yield was 47.1%.

MS (ESI): [M+H]+=374

1H-NMR (400 MHz, DMSO-d6) δppm: 4.80 (s, 2H), 6.62 (t, H, J=7.2 Hz), 6.80 (d, 1H, J=8.0 Hz), 6.98 (t, 1H, J=7.6 Hz), 7.20 (d, 1H, J=8.0 Hz), 7.81-8.11 (m, 6H), 8.49 (dd, 1H, J=2.4 Hz, 6.4 Hz), 8.69 (s, 1H), 9.58 (s, 1H), 9.89 (s, 1H).

EXAMPLE 14

V-14 N-(2-amino-5-fluorophenyl)-4-(8-fluoroquinazoline-4-amino)benzamide

Following the General Method I for the preparation of the intermediate IIIa, a white solid (Intermediate M-14) of the weight 2.23 g was obtained with 8-fluoro-4-chloroquinazoline (1.82 g, 10 mmol) (prepared according to General Method III) and p-aminobenzoic acid (1.37 g, 10 mmol). The yield was 79%.

Following the General Method I for the preparation of the final product V, a white solid of the weight 0.211 g was obtained with M-14 (0.283 g, 1 mmol), 4-fluoro-1,2-phenylenediamine (0.126 g, 1 mmol), HBTU (0.379 g, 1 mmol), N,N-dimethylformamide (10 ml), and triethylamine (0.202 g, 2 mmol). The yield was 53.8%.

MS (ESI): [M+H]+=392

1H-NMR (400 MHz, DMSO-d6) δppm: 4.80 (s, 2H), 6.62 (t, 1H, J=7.2 Hz), 6.80 (d, 1H, J=8.0 Hz), 6.98 (t, 1H, J=7.6 Hz), 7.20 (d, 1H, J=8.0 Hz), 7.81-8.11 (m, 5H), 8.49 (dd, 1H, J=2.4 Hz, 6.4 Hz), 8.69 (s, 1H), 9.58 (s, 1H), 9.89 (s, 1H).

EXAMPLE 15

V-15 N-(2-aminophenyl)-4-(6,7-dimethoxyethoxyquinazoline-4-amino)benzamide

Following the General Method I for the preparation of the intermediate IIIa, a white solid (Intermediate M-15) of the weight 3.37 g was obtained with 6,7-dimethoxyethoxy-4-chloroquinazoline (3.12 g, 10 mmol) (prepared according to General Method III) and p-aminobenzoic acid (1.37 g, 10 mmol). The yield was 82%.

Following the General Method I for the preparation of the final product V, a white solid of the weight 0.311 g was obtained with M-15 (0.413 g, 1 mmol), o-phenylenediamine (0.108 g, 1 mmol), HBTU (0.379 g, 1 mmol), N,N-dimethylformamide (10 ml), and triethylamine (0.202 g, 2 mmol). The yield was 61.8%.

MS (ESI): [M+H]+=504

1H-NMR (400 MHz. DMSO-d6) δppm: 3.35 (s, 6H), 3.75 (m, 4H), 4.24 (m, 2H), 4.84 (m, 4H), 6.59 (dt, 1H, J=1.2 Hz, 7.6 Hz), 6.77 (dd, 1H, J=1.2 Hz, 8.0 Hz), 6.97 (dt, 1H, J=1.2 Hz, 7.6 Hz), 7.17 ((m, 2H), 7.48 (d, 2H, J=8.0 Hz), 7.70 (s, 1H), 7.93 (d, 2H, J=8.4 Hz), 8.31 (s, 1H), 8.47 (t, 1H, J=6.0 Hz), 9.54 (s, 1H).

EXAMPLE 16

V-16 N-(2-amino-4-pyridyl)-4-(6,7-dimethoxyethoxy quinazoline-4-amino)benzamide

Following the General Method I for the preparation of the final product V, a white solid of the weight 0.307 g was obtained with M-15 (0.413 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol). The yield was 60.8%.

MS (ESI): [M+H]+=505

1H-NMR (400 MHz, DMSO-d6) δppm: 3.31 (s, 6H), 3.74 (m, 4H), 4.23 (m, 2H), 4.82 (m, 4H), 6.55 (dt, 1H, J=2 Hz, 7.6 Hz), 6.77 (dd, 1H, J=1.2 Hz, 8.0 Hz), 6.94 (dt, 1H, J=1.2 Hz, 7.6 Hz), 7.16 ((m, 2H), 7.48 (m, 1H), 7.66 (s, 1H), 7.93 (d, 2H, J=8.4 Hz), 8.30 (s, 1H), 8.46 (t, 1H, J=6.0 Hz), 9.50 (s, 1H).

EXAMPLE 17

V-17 N-(2-aminophenyl)-4-[7-methoxy-6-(3-morpholinyl propoxy)quinazoline-4-amino]benzamide Following the General Method I for the preparation of the intermediate IIIa, a white solid (intermediate M-17) of the weight 3.03 g was obtained with 7-methoxy-6-(3-morpholinylpropoxy)-4-chloroquinazoline (3.37 g, 10 mmol) (prepared according to General Method III) and p-aminobenzoic acid (1.37 g, 10 mmol). The yield was 69%.

Following the General Method I for the preparation of the final product V, a white solid of the weight 0.409 g was obtained with M-17 (0.438 g, 1 mmol), o-phenylenediamine (0.108 g, 1 mmol), HBTU (0.379 g, 1 mmol), N,N-dimethylformamide (10 ml), and triethylamine (0.202 g, 2 mmol). The yield was 77.5%.

MS (ESI): [M+H]+=529

1H-NMR (400 MHz, DMSO-d6) δppm: 1.82 (m, 2H), 2.31-2.47 (m, 6H), 3.65 (m, 4H), 3.90 (s, 3H), 4.06 (m, 2H), 5.13 (s, 2H), 7.11 (s, 1H), 7.42 (d, 1H, J=5.2 Hz), 7.49 (d, 2H, J=8.0 Hz), 7.68 (s, 1H), 7.78 (d, 1H, J=5.2 Hz), 7.90 (d, 2H, J=8.0 Hz), 8.08 (s, 1H), 8.31 (s, 1H), 8.54 (1, 1H, J=6.0 Hz), 9.65 (s, 1H).

EXAMPLE 18

V-18 N-(2-amino-5-fluorophenyl)-4-[7-methoxy-6-(3-morpholinylpropoxy)quinazoline-4-amino)benzamide Following the General Method I for the preparation of the final product V, a white solid of the weight 0.334 g was obtained with M-17 (0.438 g, 1 mmol), 4-fluoro-1,2-phenylenediamine (0.126 g, 1 mmol), HBTU (0.379 g, 1 mmol), N,N-dimethylformamide (10 ml), and triethylamine (0.202 g, 2 mmol). The yield was 61.2%.

MS (ESI): [M+H]+=547

1H-NMR (400 MHz, DMSO-d6) δppm: 1.80 (m, 2H), 2.35-2.51 (m, 6H), 3.69 (m, 4H), 3.90 (s, 3H), 4.05 (m, 2H), 5.10 (s, 2H), 7.41 (d, 1H, J=5.6 Hz), 7.49 (d, 2H, J=8.0 Hz), 7.68 (s, 1H), 7.78 (d, 1H, J=5.6 Hz), 7.90 (d, 2H, J=8.0 Hz), 8.06 (s, 1H), 8.41 (s, 1H), 8.54 (t, 1H, J=6.0 Hz), 9.77 (s, 1H).

EXAMPLE 19

V-19 N-(2-aminophenyl)-4-[6-(5-((2-(methylsulfonyl)ethylamino)methyl)furyl)quinazoline-4-amino]benzamide Following the General Method I for the preparation of the intermediate IIIa, a white solid (Intermediate M-19) of the weight 3.75 g was obtained with 6-(5-((2-(methylsulfonyl)ethylamino)methyl)furyl)-4-chloroquinazoline (3.65 g, 10 mmol) (prepared according to General Method III) and p-aminobenzoic acid (1.37 g, 10 mmol). The yield was 80%.

Following the General Method I for the preparation of the final product V, a white solid of the weight 0.319 g was obtained with M-19 (0.466 g, 1 mmol), o-phenylenediamine (0.108 g, 1 mmol), HBTU (0.379 g, 1 mmol), N,N-dimethylformamide (10 ml), and triethylamine (0.202 g, 2 mmol). The yield was 57.4%.

MS (ESI): [M+H]+=557

1H-NMR (400 MHz, DMSO-d6) δppm: 2.83 (s, 3H), 3.11 (m, 2H), 3.53 (m, 2H), 3.66 (d, 1H, J=5.6 Hz), 5.19 (s, 2H), 6.26 (m, 1H), 6.79 (m, 1H), 6.99-7.01 (m, 2H), 7.41 (d, 1H, J=5.6 Hz), 7.49 (d, 2H, J=8.0 Hz), 7.70 (m, 2H), 7.92-8.06 (m, 3H), 8.22 (m, 1H), 8.49 (s, 1H), 9.21 (s, 1H), 9.67 (s, 1H).

EXAMPLE 20

V-20 N-(2-amino-5-fluorophenyl)-4-[6-(5-((2-(methyl sulfonyl)ethylamino)methyl)furyl)quinazoline-4-amino)]benzamide Following the General Method I for the preparation of the final product V, a white solid of the weight 0.298 g was obtained with M-19 (0.466 g, 1 mmol), 4-fluoro-1,2-phenylenediamine (0.126 g, 1 mmol), HBTU (0.379 g, 1 mmol), N,N-dimethylformamide (10 ml), and triethylamine (0.202 g, 2 mmol). The yield was 51.8%.

MS (ESI): [M+H]+=575

1H-NMR (400 MHz, DMSO-d6) δppm: 2.85 (s, 3H), 3.11 (m, 2H), 3.53 (m, 2H), 3.67 (d., H, J=5.6 Hz), 5.19 (s, 2H), 6.26 (m, 1H), 6.59 (m, 1H), 6.73 (m, 1H), 7.01 (m, 1H), 7.45-7.53 (m, 3H), 7.70 (m, 2H), 8.06 (m, 2H), 8.22 (m, 1H), 8.49 (s, 1H), 9.21 (s, 1H), 9.60 (s, 1H).

EXAMPLE 21

V-21 N-(2-aminophenyl)-4-(6-acetamidoquinazoline-4-amino)benzamide

Following the General Method I for the preparation of the intermediate IIIa, a white solid (Intermediate M-21) of the weight 2.71 g was obtained with 6-acetamido-4-chloroquinazoline (2.21 g, 10 mmol) (prepared according to General Method III) and p-aminobenzoic acid (1.37 g, 10 mmol). The yield was 84%.

Following the General Method I for the preparation of the final product V, a white solid of the weight 0.248 g was obtained with M-21 (0.322 g, 1 mmol), o-phenylenediamine (0.108 g, 1 mmol), HBTU (0.379 g, 1 mmol), N,N-dimethylformamide (10 ml), and triethylamine (0.202 g, 2 mmol). The yield was 60.2%.

MS (ESI): [M+H]+=413

1H-NMR (400 MHz, DMSO-d6) δppm: 2.04 (s, 3H), 4.84 (m, 2H), 6.59 (dt, 1H, J=1.2 Hz, 7.2 Hz), 6.77 (dd, 1H, J=1.2 Hz, 8.0 Hz), 6.96 (dt, 1H, J=1.2 Hz, 8.0 Hz), 7.17 (dd, 1H, J=1.2 Hz, 8.0 Hz), 7.49 (d, 2H, J=8.4 Hz), 7.72 (d, 1H, J=8.8 Hz), 7.79 (dd, 1H, J=1.2 Hz, 8.8 Hz), 7.93 (d, 2H, J=8.0 Hz), 8.48 (m, 2H), 8.94 (t, 1H, J=5.6 Hz), 9.55 (s, 1H), 10.71 (s, 1H).

EXAMPLE 22

V-22 N-(2-aminophenyl)-4-(6-methoxycarbonylmethyl quinazoline-4-amino)benzamide

Following the General Method I for the preparation of the intermediate IIIa, a white solid (Intermediate M-22) of the weight 2.11 g was obtained with 6-methoxycarbonylmethyl-4-chloroquinazoline (2.36 g, 10 mmol) (prepared according to General Method III) and p-aminobenzoic acid (1.37 g, 10 mmol). The yield was 63%.

Following the General Method I for the preparation of the final product V, a white solid of the weight 0.201 g was obtained with M-22 (0.337 g, 1 mmol), o-phenylenediamine (0.108 g, 1 mmol), HBTU (0.379 g, 1 mmol), N,N-dimethylformamide (10 ml), and triethylamine (0.202 g, 2 mmol). The yield was 47.1%.

MS (ESI): [M+H]+=428

1H-NMR (400 MHz, DMSO-d6) δppm: 3.63-3.75 (m, 6H), 5.19 (s, 2H), 6.79 (m, 1H), 6.98 (m, 1H), 7.40 (d, 1H, J=5.6 Hz), 7.53 (m, 2H), 7.68-7.81 (m, 4H), 8.00 (m, 1H), 8.49 (s, 1H), 9.21 (s, 1H), 9.51 (s, 1H).

EXAMPLE 23

V-23 N-[2-amino-5-(2-thienyl)phenyl]-4-(6,7-dimethoxy quinazoline-4-amino)benzamide Following the General Method I for the preparation of the final product V, a white solid of the weight 0.243 g was obtained with M-4 (0.325 g, 1 mmol), 4-(2-thienyl)-1,2-phenylenediamine (0.190 g, 1 mmol), HBTU (0.379 g, 1 mmol), N,N-dimethylformamide (10 ml), and triethylamine (0.202 g, 2 mmol). The yield was 49.9%.

MS (ESI): [M+H]+=498

1H-NMR (400 MHz, DMSO-d6) δppm: 3.90 (s, 6H) 5.13 (s, 2H), 7.11 (s, 1H), 7.42 (d, 1H, J=5.2 Hz), 7.49-7.68 (m, 3H), 7.78 (d, 1H, J=5.2 Hz), 7.90 (d, 2H, J=8.0 Hz), 8.08 (s, 1H), 8.31 (s, 1H), 8.44 (t, 1H, J=6.0 Hz), 9.67 (s, 1H).

EXAMPLE 24

V-24 N-[2-amino-5-(phenyl)phenyl]-4-(6,7-dimethoxy quinazoline-4-amino)benzamide Following the General Method I for the preparation of the final product V, a white solid of the weight 0.198 g was obtained with M-4 (0.325 g, 1 mmol), 4-phenyl-1,2-phenylenediamine (0.184 g, 1 mmol), HBTU (0.379 g, 1 mmol), N,N-dimethylformamide (10 ml), and triethylamine (0.202 g, 2 mmol). The yield was 40.3%.

MS (ESI): [M+H]+=492

1H-NMR (400 MHz, DMSO-d6) δppm: 3.83 (s, 6H), 5.19 (s, 2H), 6.60 (m, 1H), 7.22-7.29 (m, 2H), 7.40-7.61 (m, 8H), 7.71 (m, 2H), 7.84 (s, 1H), 8.49 (s, 1H), 9.21 (s, 1H), 9.51 (s, 1H).

EXAMPLE 25

V-25 N-[2-amino-5-(2-furyl)phenyl]-4-(6,7-dimethoxy quinazoline-4-amino)benzamide Following the General Method I for the preparation of the final product V, a white solid of the weight 0.104 g was obtained with M-4 (0.325 g, 1 mmol), 4-(2-furyl)-1,2-phenylenediamine (0.174 g, 1 mmol), HBTU (0.379 g, 1 mmol), N,N-dimethylformamide (10 ml), and triethylamine (0.202 g, 2 mmol). The yield was 21.6%.

MS (ESI): [M+H]+=482

1H-NMR (400 MHz, DMSO-d6) δppm: 3.92 (s, 6H) 5.11 (s, 2H), 7.13 (s, 1H), 7.42 (d, 1H, J=5.2 Hz), 7.49-7.68 (m, 3H), 7.78 (d, 1H, J=5.2 Hz), 7.90 (d, 2H, J=8.0 Hz), 8.08 (s, 1H), 8.30 (s, 1H), 8.41 (t, 1H, J=6.0 Hz), 9.65 (s, 1H).

EXAMPLE 26

V-26 N-(2-amino-4-pyridyl)-4-((quinazoline-4-amino)methyl benzamide

Following the General

Method II for the preparation of the intermediate IIIc, a white solid (Intermediate M-26) of the weight 2.01 g was obtained with 4-chloroquinazoline (1.64 g, 10 mmol) and methyl 4-(aminomethyl)benzoate hydrochloride (2.22 g, 11 mmol). The yield was 72%.

Following the General Method II for the preparation of the final product V, a white solid of the weight 0.234 g was obtained with M-26 (0.279 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol). The yield was 63.3%.

MS (ESI): [M+H]+=371

1H-NMR (400 MHz, DMSO-d6) δppm: 3.90 (s, 6H), 4.85 (d, 2H, J=5.6 Hz), 5.13 (s, 2H), 7.11 (s, 1H), 7.42 (d, 1H, J=5.2 Hz), 7.49 (d, 2H, J=8.0 Hz), 7.68 (s, 1H), 7.78 (d, 1H, J=5.2 Hz), 7.90) (d, 2H, J=8.0 Hz), 8.08 (s, 1H), 8.31 (s, 1H), 8.54 (t, 1H, J=6.0 Hz), 9.65 (s, 1H)

EXAMPLE 27

V-27 N-(2-aminophenyl)-4-[(quinazoline-4-amino)methyl]benzamide

Following the General Method II for the preparation of the final product V, a white solid of the weight 0.177 g was obtained with M-26 (0.279 g, 1 mmol), o-phenylenediamine (0.108 g, 1 mmol), HBTU (0.379 g, 1 mmol), N,N-dimethylformamide (10 ml), and triethylamine (0.202 g, 2 mmol). The yield was 47.8%.

MS (ESI): [M+H]+=370

1H-NMR (400 MHz, DMSO-d6) δppm: 4.82 (s, 2H), 4.86 (d, 2H, J=6.0 Hz), 6.59 (t, 1H, J=7.4 Hz), 6.77 (d, 2H, J=6.8 Hz), 6.55 (dt, 1H, J=1.2 Hz, 7.6 Hz), 7.17 (d, 1H, J=7.6 Hz), 7.48 (d, 2H, J=8.0 Hz), 7.55 (t, 1H, J=8.0 Hz), 7.71 (d, 1H, J=8.4 Hz), 7.79 (t, 1H, J=8.0 Hz), 7.92 (d, 2H, J=8.0 Hz), 8.31 (d, 1H, J=8.0 Hz), 8.45 (s, 1H), 8.86 (t, 1H, J=6.0 Hz), 9.53 (s, 1H)

EXAMPLE 28

V-28 N-[2-amino-5-(2-thienyl)phenyl]-4-[(quinazoline-4-amino)methyl]benzamide Following the General Method II for the preparation of the final product V, a white solid of the weight 0.219 g was obtained with M-26 (0.279 g, 1 mol), 4-(2-thienyl)-1,2-phenylenediamine (0.190 g, 1 mmol), HBTU (0.379 g, 1 mmol), N,N-dimethylformamide (10 ml), and triethylamine (0.202 g, 2 mmol). The yield was 48.5%.

MS (ESI): [M+H]+=452

1H-NMR (400 MHz, DMSO-d6) δppm: 4.81 (s, 2H), 4.86 (d, 2H, J=5.6 Hz), 6.57 (t, 1H, J=7.4 Hz), 6.77 (d, 2H, J=6.4 Hz), 6.55 (dt, 1H, J=1.2 Hz, 7.6 Hz), 7.17 (d, 1H, J=7.6 Hz), 7.48-7.69 (m, 3H), 7.71 (d, 1H, J=8.4 Hz), 7.79 (t, 1H, J=8.0 Hz), 7.92 (d, 2H, J=8.0 Hz), 8.31 (d, 1H, J=8.0 Hz), 8.45 (s, 1H), 8.86 (t, 1H, J=6.0 Hz), 9.53 (s, 1H)

EXAMPLE 29

V-29 N-(2-amino-5-fluorophenyl)-4-[(quinazoline-4-amino)methyl]benzamide

Following the General Method II for the preparation of the final product V, a white solid of the weight 0.208 g was obtained with M-26 (0.279 g, 1 mmol), 4-fluoro-1,2-phenylenediamine (0.126 g, 1 mmol), HBTU (0.379 g, 1 mmol), N,N-dimethylformamide (10 ml), and triethylamine (0.202 g, 2 mmol). The yield was 53.6%.

MS (ESI): [M+H]+=388

1H-NMR (400 MHz, DMSO-d6) δppm: 4.85 (d, 2H, J=6.4 Hz), 5.17 (s, 2H), 6.35 (dt, 1H, J=2.8 Hz, 8.4 Hz), 6.52 (dd, 1H, J=2.8 Hz, 11.2 Hz), 7.10 (dt, 1H. J=2.0 Hz, 8.4 Hz), 7.46 (d, 2H, J=7.6 Hz), 7.55 (t, 11, J=7.4 Hz), 7.70 (d, 1H, J=7.6 Hz), 7.79 (t, 1H, J=7.6 Hz), 7.91 (d, 2H, J=8.0 Hz), 8.31 (d, 11, J=7.6 Hz), 8.44 (s, 1H), 8.90 (t, 1H, J=6.0 Hz), 9.50 (s, 1H)

EXAMPLE 30

V-30 N-(2-amino-4-pyridyl)-4-[(6,7-dimethoxyquinazoline-4-amino)methyl]benzamide Following the General Method II for the preparation of the intermediate IIIc, a white solid (Intermediate M-30) of the weight 2.01 g was obtained with 6,7-dimethoxy-4-chloroquinazoline (2.24 g, 1 (10 mol) and methyl 4-(aminomethyl)benzoate hydrochloride (2.22 g, 11 mmol). The yield was 59%.

Following the General Method II for the preparation of the final product V, a white solid of the weight 0.275 g was obtained with M-30 (0.339 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol). The yield was 63.9%.

MS (ESI): [M+H]+=431

1H-NMR (400 MHz, DMSO-d6) δppm: 3.90 (s, 6H), 4.85 (d, 2H, J=5.6 Hz), 5.13 (s, 2H), 7.11 (s, 1H), 7.42 (d, 1H, J=5.2 Hz), 7.49 (d, 211, J=8.0 Hz), 7.68 (s, 1H), 7.78 (d, 1H, J=5.2 Hz), 7.92 (d, 2H, J=8.0 Hz), 8.08 (s, 1H), 8.31 (s, 1H), 8.54 (t, 1H, J=6.0 Hz), 9.65 (s, 1H)

EXAMPLE 31

V-31 N-[2-amino-5-(2-thienyl)phenyl]-4-[(6,7-dimethoxyquinazoline-4-amino)methyl]benzamide Following the General Method II for the preparation of the final product V, a white solid of the weight 0.231 g was obtained with M-30 (0.339 g, 1 mmol), 4-(2-thienyl)-1,2-phenylenediamine (0.190 g, 1 mmol). HBTU (0.379 g, 1 mmol), N,N-dimethylformamide (10 ml), and triethylamine (0.202 g, 2 mmol). The yield was 45.1%.

MS (ESI): [M+H]+=512

1H-NMR (400 MHz, DMSO-d6) δppm: 3.90 (s, 6H), 4.85 (d, 2H, J=5.6 Hz), 5.13 (s, 2H), 7.11 (s, 1H), 7.42 (d, 1H, J=5.2 Hz), 7.49-7.68 (m, 3H), 7.78 (d, H, J=5.2 Hz), 7.90 (d, 2H, J=8.0 Hz), 8.08 (s, 1H), 8.31 (s, 1H), 8.44 (t, 1H, J=6.0 Hz), 9.67 (s, 1H)

EXAMPLE 32

V-32 N-(2-aminophenyl)-4-[(7-methoxyquinazoline-4-amino)methyl]benzamide

Following the General Method II for the preparation of the intermediate IIIc, a white solid (Intermediate M-32) of the weight 2.11 g was obtained with 7-methoxy-4-chloroquinazoline (1.94 g, 10 mmol) (prepared according to General Method III) and methyl 4-(aminomethyl)benzoate hydrochloride (2.22 g, 11 mmol). The yield was 68.3%.

Following the General Method II for the preparation of the final product V, a white solid of the weight 0.198 g was obtained with M-32 (0.309 g, 1 mmol), o-phenylenediamine (0.108 g, 1 mmol), HBTU (0.379 g, 1 mmol), N,N-dimethylformamide (10 ml), and triethylamine (0.202 g, 2 mmol). The yield was 49.6%.

MS (ESI): [M+H]+=400

1H-NMR (400 MHz, DMSO-d6) δppm: 3.86 (s, 3H), 4.84 (d, 2H, J=5.6 Hz), 5.13 (s, 2H), 7.11 (m, 2H), 7.43 (d, 1H, J=6.0 Hz), 7.47 (d, 2H, J=8.0 Hz), 7.68 (s, 1H), 7.76 (d, 1H, J=5.2 Hz), 7.90 (d, 2H, J=8.0 Hz), 8.07 (s, 1H), 8.33 (s, 1H), 8.51 (t, 1H, J=6.0 Hz), 9.69 (s, 1H)

EXAMPLE 33

V-33 N-(2-aminophenyl)-4-[(6-methoxyquinazoline-4-amino)methyl]benzamide

Following the General Method II for the preparation of the intermediate IIIc, a white solid (Intermediate M-33) of the weight 2.01 g was obtained with 6-methoxy-4-chloroquinazoline (1.94 g, 10 mmol) (prepared according to General Method III) and methyl 4-(aminomethyl)benzoate hydrochloride (2.22 g, 11 mmol). The yield was 65%.

Following the General Method II for the preparation of the final product V, a white solid of the weight 0.177 g was obtained with M-33 (0.309 g, 1 mmol), o-phenylenediamine (0.108 g, 1 mmol). HBTU (0.379 g, 1 mmol), N,N-dimethylformamide (10 ml), and triethylamine (0.202 g, 2 mmol). The yield was 44.4%.

MS (ESI): [M+H]+=400

1H-NMR (400 MHz, DMSO-d6) δppm: 3.92 (s, 3H), 4.81 (d, 2H, J=5.6 Hz), 5.13 (s, 2H), 7.11 (s, 1H), 7.35-7.43 (m, 2H), 7.47 (d, 2H, J=8.0 Hz), 7.68 (s, 1H), 7.76 (d, 1H, J=5.2 Hz), 7.92 (d, 2H, J=8.0 Hz), 8.11 (s, 1H), 8.39 (s, 1H), 8.51 (t, 1H, J=6.0 Hz), 9.70 (s, 1H)

EXAMPLE 34

V-34 N-(2-aminophenyl)-4-[(8-methoxyquinazoline-4-amino)methyl]benzamide

Following the General Method II for the preparation of the intermediate IIIc, a white solid (Intermediate M-34) of the weight 1.98 g was obtained with 8-methoxy-4-chloroquinazoline (1.94 g, 10 mmol) (prepared according to General Method III) and methyl 4-(aminomethyl)benzoate hydrochloride (2.22 g, 11 mmol). The yield was 64%.

Following the General Method II for the preparation of the final product V, a white solid of the weight 0.154 g was obtained with M-34 (0.309 g, 1 mmol), o-phenylenediamine (0.108 g, 1 mmol), HBTU (0.379 g, 1 mmol), N,N-dimethylformamide (10 ml), and triethylamine (0.202 g, 2 mmol). The yield was 38.6%.

MS (ESI): [M+H]+=400

1H-NMR (400 MHz, DMSO-d6) δppm: 3.90 (s, 3H), 4.85 (d, 2H, J=6.0 Hz), 5.13 (s, 2H), 7.11 (s, 1H), 7.32-7.42 (m, 2H), 7.47 (d, 2H, J=7.6 Hz), 7.67 (s, 1H), 7.78 (d, 1H, J=5.2 Hz), 7.90 (d, 2H, J=8.0 Hz), 8.08 (s, 1H), 8.31 (s, 1H), 8.44 (t, 1H, J=6.0 Hz), 9.67 (s, 1H)

EXAMPLE 35

V-35 N-(2-amino-5-fluorophenyl)-4-[(8-methoxyquinazoline-4-amino)methyl]benzamide Following the General Method II for the preparation of the final product V, a white solid of the weight 0.204 g was obtained with M-34 (0.309 g, 1 mmol), 4-fluoro-1,2-phenylenediamine (0.126 g, 1 mmol), HBTU (0.379 g, 1 mmol), N,N-dimethylformamide (10 ml), and triethylamine (0.202 g, 2 mmol). The yield was 48.9%.

MS (ESI): [M+H]+=418

1H-NMR (400 MHz, DMSO-d6) δppm: 3.84 (s, 3H), 4.85 (d, 2H, J=5.6 Hz), 5.13 (s, 2H), 7.06 (s, 1H), 7.38-7.42 (m, 1H), 7.47 (d, 211, J=7.6 Hz), 7.67 (s, 1H), 7.78 (d, 1H, J=4.8 Hz), 7.90 (d, 2H, J=8.0 Hz), 8.08 (s, 1H), 8.31 (s, 1H), 8.36 (t, 1H, J=5.6 Hz), 9.61 (s, 1H)

EXAMPLE 36

V-36 N-(2-amino-5-(phenyl)phenyl)-4-[(8-methoxy quinazoline-4-amino)methyl]benzamide Following the General Method II for the preparation of the final product V, a white solid of the weight 0.287 g was obtained with M-34 (0.309 g, 1 mmol), 4-phenyl-1,2-phenylenediamine (0.184 g, 1 mmol), HBTU (0.379 g, 1 mmol), N,N-dimethylformamide (10 ml), and triethylamine (0.202 g, 2 mmol). The yield was 60.3%.

MS (ESI): [M+H]+=476

1H-NMR (400 MHz, DMSO-d6) δppm: 3.91 (s, 3H), 4.82 (d, 2H, J=6.0 Hz), 5.13 (s, 2H), 7.17 (s, 1H), 7.32-7.42 (m, 7H), 7.47 (d, 2H, J=7.6 Hz), 7.65 (s, 1H), 7.78 (d, 1H, J=5.2 Hz), 7.90 (d, 2H, J=8.0 Hz), 8.08 (s, 1H), 8.31 (s, 1H), 8.44 (t, 1H, J=6.0 Hz), 9.67 (s, 1H)

EXAMPLE 37

V-37 N-(2-aminophenyl)-4-[(6-nitroquinazoline-4-amino)methyl]benzamide

Following the General Method II for the preparation of the intermediate IIIc, a yellow solid (Intermediate M-37) of the weight 1.11 g was obtained with 6-nitro-4-chloroquinazoline (2.09 g, 10 mmol) (prepared according to General Method III) and methyl 4-(aminomethyl)benzoate hydrochloride (2.22 g, 11 mmol). The yield was 34.3%.

Following the General Method II for the preparation of the final product V, a yellow solid of the weight 0.210 g was obtained with M-37 (0.324 g, 1 mmol), o-phenylenediamine (0.108 g, 1 mmol), HBTU (0.379 g, 1 mmol), N,N-dimethylformamide (10 ml), and triethylamine (0.202 g, 2 mmol). The yield was 50.7%.

MS (ESI): [M+H]+=415

1H-NMR (400 MHz, DMSO-d6) δppm: 4.87 (s, 2H), 5.17 (m, 2H) 6.62 (dt, 1H, J=1.2 Hz, 8.0 Hz), 6.79 (dd, 1H, J=1.2 Hz, 8.0 Hz), 6.98 (dt, 1H, J=1.2 Hz, 8.0 Hz), 7.21 (d, 1H, J=8.0 Hz), 7.97-8.08 (m, 5H), 8.58 (dd, 1H, J=2.4 Hz, 9.2 Hz), 8.80 (s, 1H), 9.59 (s, 1H), 9.70 (d, 1H, J=1.6 Hz), 10.57 (s, 1H)

EXAMPLE 38

V-38 N-(2-aminophenyl)-4-[(6,7-dimethoxyethoxy quinazoline-4-amino)methyl]benzamide Following the General Method II for the preparation of the intermediate IIIc, a white solid (Intermediate M-38) of the weight 1.11 g was obtained with 6,7-dimethoxyethoxy-4-chloroquinazoline (3.12 g, 10 mmol) (prepared according to General Method III) and methyl 4-(aminomethyl)benzoate hydrochloride (2.22 g, 11 mmol). The yield was 34.3%.

Following the General Method II for the preparation of the final product V, a white solid of the weight 0.267 g was obtained with M-38 (0.427 g, 1 mmol), o-phenylenediamine (0.108 g, 1 mmol), HBTU (0.379 g, 1 mmol), N,N-dimethylformamide (10 ml), and triethylamine (0.202 g, 2 mmol). The yield was 51.7%.

MS (ESI): [M+H]+=518

1H-NMR (400 MHz, DMSO-d6) δppm: 3.35 (s, 6H), 3.75 (m, 4H), 4.24 (m, 4H), 4.84 (m, 4H), 6.59 (dt, 1H, J=1.2 Hz, 7.6 Hz), 6.77 (dd, 1H, J=1.2 Hz, 8.0 Hz), 6.97 (dt, 1H, J=1.2 Hz, 7.6 Hz), 7.17 ((m, 2H), 7.48 (d, 2H, J=8.0 Hz), 7.70 (s, 1H), 7.93 (d, 2H, J=8.4 Hz), 8.31 (s, 1H), 8.47 (t, 1H, J=6.0 Hz), 9.54 (s, 1H)

EXAMPLE 39

V-39 N-(2-amino-4-pyridyl)-4-[(6,7-dimethoxyethoxy quinazoline-4-amino)methyl]benzamide Following the General Method II for the preparation of the final product V, a white solid of the weight 0.207 g was obtained with M-38 (0.427 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol). The yield was 40.0%.

MS (ESI): [M+H]+=519

1H-NMR (400 MHz, DMSO-d6) δppm: 3.32 (s, 6H), 3.72 (m, 4H), 4.14 (m, 4H), 4.83 (m, 4H), 6.52 (dt, 1H, J=1.2 Hz, 7.2 Hz), 6.97 (dt, 1H, J=1.2 Hz, 7.2 Hz), 7.13 ((m, 2H), 7.48 (d, 2H, J=8.0 Hz), 7.72 (s, 1H), 7.91 (d, 2H, J=8.4 Hz), 8.30 (s, 1H), 8.45 (t, 1H, J=6.0 Hz), 9.56 (s, 1H)

EXAMPLE 40

V-40 N-(2-amino-5-fluorophenyl)-4-[(6,7-dimethoxyethoxy quinazoline-4-amino)methyl]benzamide Following the General Method II for the preparation of the final product V, a white solid of the weight 0.246 g was obtained with M-38 (0.427 g, 1 mmol), 4-fluoro-1,2-phenylenediamine (0.126 g, 1 mmol), HBTU (0.379 g, 1 mmol), N,N-dimethylformamide (10 ml), and triethylamine (0.202 g, 2 mmol). The yield was 45.9%.

MS (ESI): [M+H]+=536

1H-NMR (400 MHz, DMSO-d6) δppm: 3.34 (s, 6H), 3.75 (m, 4H), 4.14 (m, 4H), 4.82 (m, 4H), 6.52 (dt, 1H, J=1.2 Hz, 7.2 Hz), 6.99 (dt, 1H, J=1.2 Hz, 7.2 Hz), 7.13 ((m, 2H), 7.49 (d, 2H, J=8.0H-z), 7.73 (s, 1H), 7.93 (d, 2H, J=8.4 Hz), 8.37 (s, 1H), 8.46 (t, 1H, J=6.0 Hz), 9.55 (s, 1H)

EXAMPLE 41

V-41 N-(2-aminophenyl)-4-[(7-methoxy-6-(3-morpholinyl propoxy)quinazoline-4-amino)methyl]benzamide Following the General Method II for the preparation of the intermediate IIIc, a white solid (Intermediate M-41) of the weight 2.98 g was obtained with 7-methoxy-6-(3-morpholinylpropoxy)-4-chloroquinazoline (3.37 g, 10 mmol) (prepared according to General Method III) and methyl 4-(aminomethyl)benzoate hydrochloride (2.22 g, 11 mmol). The yield was 65.9%.

Following the General Method II for the preparation of the final product V, a white solid of the weight 0.222 g was obtained with M-41 (0.452 g, 1 mmol), o-phenylenediamine (0.108 g, 1 mmol), HBTU (0.379 g, 1 mmol), N,N-dimethylformamide (10 ml), and triethylamine (0.202 g, 2 mmol). The yield was 41.0%.

MS (ESI): [M+H]+=543

1H-NMR (400 MHz, DMSO-d6) δppm: 1.82 (m, 2H), 2.31-2.47 (m, 6H), 3.65 (m, 4H), 3.90 (s, 3H), 4.84 (m, 4H), 6.59 (dt, 1H, J=1.2 Hz, 7.6 Hz), 6.77 (dd, 1H, J=1.2 Hz, 8.0 Hz), 6.97 (dt, 1H, J=1.2 Hz, 8.0 Hz), 7.09 (s, 1H), 7.13 (d, 1H, J=8.0 Hz), 7.46 (d, 2H, J=8.4 Hz), 7.62 (s, 1H), 7.88 (d, 2H, J=8.0 Hz), 8.28 (s, 1H), 8.48 (t, 1H, J=5.6 Hz), 9.53 (s, 1H)

EXAMPLE 42

V-42 N-(2-amino-4-pyridyl)-4-[(7-methoxy-6-(3-morpholinyl propoxy)quinazoline-4-amino)methyl] benzamide Following the General Method II for the preparation of the final product V, a white solid of the weight 0.211 g was obtained with M-41 (0.452 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol). The yield was 38.9%.

MS (ESI): [M+H]+=544

1H-NMR (400 MHz, DMSO-d6) δppm: 1.84 (m, 2H), 2.31-2.47 (m, 6H), 3.67 (m, 4H), 3.90 (s, 3H), 4.84 (m, 4H), 6.59 (dt, 1H, J=1.2 Hz, 7.6 Hz) 6.99 (dt, 1H, J=1.2 Hz, 8.0 Hz), 7.09 (s, 1H), 7.13 (d, 1H, J=8.0 Hz), 7.46 (d, 2H, J=8.4 Hz), 7.61 (s, 1H), 7.82 (d, 2H, J=8.0 Hz), 8.27 (s, 1H), 8.49 (t, 1H, J=5.6 Hz), 9.55 (s, 1H)

EXAMPLE 43

V-43 N-(2-aminophenyl)-4-[(8-fluoroquinazoline-4-amino)methyl]benzamide

Following the General Method II for the preparation of the intermediate IIIc, a white solid (Intermediate M-43) of the weight 1.91 g was obtained with 8-fluoro-4-chloroquinazoline (1.82 g, 10 mmol) (prepared according to General Method III) and methyl 4-(aminomethyl)benzoate hydrochloride (2.22 g, 11 mmol). The yield was 64.3%.

Following the General Method II for the preparation of the final product V, a white solid of the weight 0.119 g was obtained with M-43 (0.297 g, 1 mmol), o-phenylenediamine (0.108 g, 1 mmol), HBTU (0.379 g, 1 mmol), N,N-dimethylformamide (10 ml), and triethylamine (0.202 g, 2 mmol). The yield was 30.7%.

MS (ESI): [M+H]+=388

1H-NMR (400 MHz, DMSO-d6) δppm: 4.85 (m, 4H), 6.59 (dt, 1H, J=1.2 Hz, 7.6 Hz), 6.77 (dd, 1H, J=1.2 Hz, 8.0 Hz), 6.96 (dt, 1, J=1.2 Hz, 8.0 Hz), 7.17 (dd, 1H, J=1.2 Hz, 7.6 Hz), 7.48 (d, 2H, J=8.4 Hz), 7.59 (dd, 1H, J=2.0 Hz, 8.8 Hz), 7.75 (d, 1H, J=2.4 Hz), 7.93 (d, 1, J=8.0 Hz), 8.35 (d, 1H, J=8.8 Hz), 8.47 (s, 1H), 9.00 (t, 1H, J=5.6 Hz), 9.54 (s, 1H)

EXAMPLE 44

V-44 N-(2-amino-4-pyridyl)-4-[(8-fluoroquinazoline-4-amino)methyl]benzamide

Following the General Method II for the preparation of the final product V, a white solid of the weight 0.153 g was obtained with M-43 (0.297 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol). The yield was 39.3%.

MS (ESI): [M+H]+=389

1H-NMR (400 MHz, DMSO-d6) δppm: 4.85 (d, 2H, J=6.0 Hz), 5.17 (s, 2H), 6.35 (dt, 1H, J=2.8 Hz, 8.4 Hz), 6.53 (dd, 1H, J=2.8 Hz, 7.2 Hz), 7.10 (dt, 1H, J=1.6 Hz, 6.8 Hz), 7.46 (d, 2H, J=8.0 Hz), 7.60 (dd, 1H, J=2.4 Hz, 4.8 Hz), 7.74 (d, 1H, J=2.0 Hz), 7.91 (d, 2H, J=8.0 Hz), 8.35 (d, 1H, J=8.8 Hz), 8.46 (s, 1H), 9.04 (t, 1H, J=6.0 Hz), 9.51 (s, 1H)

EXAMPLE 45

V-45 N-(2-amino-5-(2-furyl)phenyl]-4-[(8-fluoroquinazoline-4-amino)methyl]benzamide Following the General Method II for the preparation of the final product V, a white solid of the weight 0.257 g was obtained with M-43 (0.297 g, 1 mmol), 4-(2-furyl)-1,2-phenylenediamine (0.174 g, 1 mmol), HBTU (0.379 g, 1 mmol), N,N-dimethylformamide (10 ml), and triethylamine (0.202 g, 2 mmol). The yield was 56.6%.

MS (ESI): [M+H]+=454

1H-NMR (400 MHz, DMSO-d6) δppm: 4.86 (d, 2H, J=5.6 Hz), 5.13 (s, 2H), 7.42 (d, 2H, J=5.2 Hz), 7.50 (m, 5H,), 7.60 (dd, 1H, J=2.0 Hz, 8.8 Hz), 7.50-7.80 (m, 2H), 7.90 (d, 2H, J=8.0 Hz), 8.09 (s, 1H), 8.35 (d, 1H, J=8.0 Hz), 8.46 (s, 1H), 9.06 (t, 1H, J=5.6 Hz), 9.67 (s, 1H)

EXAMPLE 46

V-46 N-(2-aminophenyl)-4-[(6-acetamidoquinazoline-4-amino)methyl]benzamide

Following the General Method II for the preparation of the intermediate IIIc, a white solid (Intermediate M-46) of the weight 2.09 g was obtained with 6-acetamido-4-chloroquinazoline (2.21 g, 10 mmol) (prepared according to General Method II) and methyl 4-(aminomethyl)benzoate hydrochloride (2.22 g, 11 mmol). The yield was 62.2%.

Following the General Method II for the preparation of the final product V, a white solid of the weight 0.119 g was obtained with M-46 (0.336 g, 1 mmol), o-phenylenediamine (0.108 g, 1 mmol), HBTU (0.379 g, 1 mmol), N,N-dimethylformamide (10 ml), and triethylamine (0.202 g, 2 mmol). The yield was 30.7%.

MS (ESI): [M+H]+=427

1H-NMR (400 MHz, DMSO-d6) δppm: 2.04 (s, 3H), 4.84 (m, 4H), 6.59 (dt, 1H, J=1.2 Hz, 7.2 Hz), 6.77 (dd, 1H, J=1.2 Hz, 8.0 Hz), 6.96 (dt, 1H, J=1.2 Hz, 8.0 Hz), 7.17 (dd, 1H, J=1.2 Hz, 8.0 Hz), 7.49 (d, 2H, J=8.4 Hz), 7.72 (d, 1H, J=8.8 Hz), 7.79 (dd, 1H, J=1.2 Hz, 8.8 Hz), 7.93 (d, 2H, J=8.0 Hz), 8.48 (m, 2H), 8.94 (t, 1H, J=5.6 Hz), 9.55 (s, 1H), 10.71 (s, 1H)

EXAMPLE 47

V-47 N-(2-amino-4-pyridyl)-4-[(6-acetamidoquinazoline-4-amino)methyl]benzamide

Following the General Method II for the preparation of the final product V, a white solid of the weight 0.107 g was obtained with M-46 (0.336 g, 1 mmol), 3,4-diaminopyridine (0.109 g, 1 mmol), HBTU (0.379 g, 1 mmol), N,N-dimethylformamide (10 ml), and triethylamine (0.202 g, 2 mmol). The yield was 25%.

MS (ESI): [M+H]+=428

1H-NMR (400 MHz, DMSO-d6) δppm: 2.11 (s, 3H), 4.82 (m, 4H), 6.57 (dt, 1H, J=1.2 Hz, 7.2 Hz), 6.96 (dt, 1H, J=1.2 Hz, 8.0 Hz), 7.19 (dd, 1H, J=1.2 Hz, 8.0 Hz), 7.49 (d, 2H, J=8.4 Hz), 7.71 (d, 1H, J=8.8 Hz), 7.79 (dd, 1H, J=1.2 Hz, 8.8 Hz), 7.93 (d, 2H, J=8.0 Hz), 8.48 (m, 2H), 8.94 (t, 1H, J=5.6 Hz), 9.54 (s, 1H), 1055 (s, 1H)

EXAMPLE 48

V-48 N-[2-amino-5-(2-furyl)phenyl]-4-[(6-acetamido quinazoline-4-amino)methyl]benzamide Following the General Method II for the preparation of the final product V, a white solid of the weight 0.247 g was obtained with M-46 (0.336 g, 1 mmol), 4-(2-furyl)-1,2-phenylenediamine (0.174 g, 1 mmol), HBTU (0.379 g, 1 mmol), N,N-dimethylformamide (10 ml), and triethylamine (0.202 g, 2 mmol). The yield was 50.1%.

MS (ESI): [M+H]+=493

1H-NMR (400 MHz. DMSO-d6) δppm: 2.04 (s, 3H), 4.84 (m, 4H), 6.59 (dt, 1H, J=1.2 Hz, 7.2 Hz), 6.78-6.96 (m, 3H), 7.17 (dd, 1H, J=1.2 Hz, 8.0 Hz), 7.45 (d, 2H, J=8.4 Hz), 7.72

(d, 1H, J=8.8 Hz), 7.81 (dd, 1H, J=1.2 Hz, 8.8 Hz), 7.93 (d, 2H, J=8.0 Hz), 8.48 (m, 2H), 8.94 (t, 1H, J=5.6 Hz), 9.55 (s, 1H), 10.71 (s, 1H)

EXAMPLE 49

The in vitro inhibitory activities of the compounds towards HDACs were tested according to the instructions in the HDAC Inhibitor Drug Screening Kit (Biovision/Catalog #K340-100).

(1) The compounds to be tested were each individually prepared as 2 mM, 200 µM and 40 µM solutions and their inhibitory activities at these concentrations were tested. Results are as follows:

TABLE 2

In vitro inhibitory effects of the compounds towards HDACs

| | Compound | 2 mM | | 200 µM | | 40 µM | |
|---|---|---|---|---|---|---|---|
| | | Inhibition percentage (%) | SD | Inhibition percentage (%) | SD | Inhibition percentage (%) | SD |
| | MS-275 | 82.2 | 0.2 | 60.5 | 0.3 | 32.5 | 0.7 |
| 1 | V-1 | 65.2 | 1.1 | 19.8 | 2.4 | 9.4 | 4.5 |
| 2 | V-2 | 77.1 | 0.5 | 28.0 | 2.3 | 17.6 | 1.6 |
| 3 | V-3 | 78.2 | 0.4 | 36.0 | 1.2 | 9.5 | 2.9 |
| 4 | V-4 | 85.3 | 4.3 | 70.3 | 1.5 | 36.3 | 4.9 |
| 5 | V-5 | 36.7 | 2.1 | 16.8 | 2.2 | 2.8 | 0.2 |
| 6 | V-6 | 87.1 | 0.2 | 58.0 | 0.9 | 34.5 | 0.8 |
| 7 | V-7 | 39.2 | 1.0 | 22.1 | 1.8 | 6.5 | 0.6 |
| 8 | V-8 | 46.2 | 0.2 | 41.1 | 0.2 | 8.9 | 5.4 |
| 9 | V-9 | 50.0 | 2.2 | 7.8 | 2.8 | 1.9 | 2.5 |
| 10 | V-10 | 77.2 | 0.1 | 32.9 | 0.7 | 12.0 | 1.7 |
| 11 | V-11 | 49.0 | 0.9 | 11.1 | 1.1 | 4.1 | 0.2 |
| 12 | V-12 | 85.2 | 1.7 | 43.0 | 3.8 | 16.8 | 0.4 |
| 13 | V-13 | 50.0 | 4.0 | 20.1 | 0.2 | 1.0 | 1.9 |
| 14 | V-14 | 94.8 | 4.4 | 67.1 | 0.3 | 46.8 | 0.6 |
| 15 | V-15 | 61.4 | 1.7 | 51.5 | 0.4 | 13.7 | 2.1 |
| 16 | V-16 | 58.6 | 1.6 | 56.8 | 0.6 | 24.8 | 0.1 |
| 17 | V-17 | 86.7 | 0.3 | 60.7 | 0.6 | 39.7 | 1.4 |
| 18 | V-18 | 66.0 | 1.9 | 56.8 | 1.1 | 30.4 | 0.3 |
| 19 | V-19 | 72.3 | 0.7 | 57.8 | 0.3 | 22.7 | 3.8 |
| 20 | V-20 | 67.5 | 1.5 | 56.9 | 1.4 | 28.2 | 0.8 |
| 21 | V-21 | 79.2 | 1.3 | 39.1 | 1.6 | 10.1 | 0.3 |
| 22 | V-22 | 84.2 | 1.3 | 47.5 | 0.3 | 19.9 | 0.8 |
| 23 | V-23 | 40.7 | 1.3 | 37.3 | 3.1 | 17.5 | 0.2 |
| 24 | V-24 | 76.1 | 0.4 | 55.2 | 0.7 | 24.2 | 0.6 |
| 25 | V-25 | 72.8 | 1.1 | 55.2 | 0.4 | 20.5 | 0.8 |
| 26 | V-26 | 82.4 | 2.0 | 40.2 | 2.6 | 11.4 | 1.1 |
| 27 | V-27 | 91.9 | 1.0 | 82.6 | 1.1 | 73.2 | 0.2 |
| 28 | V-29 | 37.8 | 1.4 | 31.0 | 1.3 | 8.6 | 1.3 |
| 29 | V-31 | 69.8 | 3.4 | 17.3 | 2.9 | 3.5 | 0.8 |
| 30 | V-32 | 42.5 | 0.4 | 3.1 | 2.4 | 2.2 | 0.5 |
| 31 | V-33 | 88.8 | 7.1 | 66.8 | 1.7 | 53.2 | 1.3 |
| 32 | V-35 | 81.8 | 0.1 | 47.8 | 0.7 | 10.1 | 1.2 |
| 33 | V-37 | 65.7 | 2.2 | 56.1 | 0.1 | 24.0 | 2.5 |
| 34 | V-39 | 85.3 | 5.7 | 58.0 | 0.1 | 34.3 | 1.1 |
| 35 | V-42 | 90.6 | 0.9 | 46.7 | 0.6 | 17.2 | 0.0 |
| 36 | V-48 | 85.0 | 1.2 | 42.2 | 2.8 | 14.0 | 2.2 |

(2) The IC$_{50}$ value of the compound was determined using a concentration gradient from 2000 µM to 7.6E-03 µM containing 10 concentrations obtained by a four times dilution method. The screening concentration range for the reference compound MS-275 was a gradient from 2000 µM to 7.6E-03 µM containing 10 concentrations. Results are as follows:

TABLE 3

IC$_{50}$ of the compounds for the in vitro inhibition of HDACs

| Compound I.D. | IC$_{50}$ value (µM) |
|---|---|
| MS-275 | 3.52 |
| V-4 | 3.29 |
| V-5 | 7.79 |
| V-6 | 1.83 |
| V-7 | 3.99 |
| V-8 | 7.76 |
| V-9 | 4.91 |
| V-10 | 1.04 |
| V-11 | 3.11 |
| V-12 | 0.92 |
| V-13 | 1.14 |
| V-14 | 3.77 |
| V-15 | 9.40 |
| V-16 | 6.89 |
| V-17 | 1.72 |
| V-18 | 1.02 |
| V-19 | 1.37 |
| V-20 | 1.22 |
| V-27 | 1.31 |
| V-33 | 1.01 |
| V-42 | 1.67 |

EXAMPLE 50

The in vitro inhibitory activities of the compounds towards the subtype HDAC1 were tested according to the instructions in the HDAC1 Inhibitor Drug Screening Kit (Biovision).

(1) The compounds to be tested were each individually prepared as 10 µM and 1 µM solutions and their inhibitory activities at these concentrations were tested.

Results are as follows:

TABLE 4

In vitro inhibitory effects of the compounds towards HDAC1

| | 10 µM | | 1 µM | |
|---|---|---|---|---|
| Compound I.D. | % Inhibition | SD | % Inhibition | SD |
| MS-275 | 76.20 | 0.25 | 46.58 | 3.86 |
| V-6 | 50.09 | 3.49 | 6.47 | 1.98 |
| V-7 | 78.37 | 1.87 | 50.13 | 5.22 |
| V-8 | 62.68 | 1.96 | 21.38 | 1.93 |
| V-9 | 58.26 | 0.12. | 33.76 | 2.14 |
| V-10 | 62.62 | 7.76 | 45.19 | 2.75 |
| V-11 | 33.38 | 0.27 | 26.18 | 7.12 |
| V-12 | 49.15 | 3.28 | 14.98 | 3.80 |
| V-13. | 83.04 | 11.24 | 53.13 | 4.44 |
| V-14 | 28.86 | 7.96 | 1.48 | 7.44 |
| V-15 | 78.84 | 0.88 | 67.08 | 9.07 |
| V-16 | 87.38 | 0.12 | 59.13 | 1.37 |
| V-17 | 76.18 | 1.90 | 53.88 | 2.83 |
| V-18 | 80.77 | 2.60 | 59.78 | 0.90 |
| V-19 | 80.25 | 2.30 | 47.64 | 4.06 |
| V-20 | 77.38 | 3.84 | 53.53 | 4.28 |
| V-21 | 86.86 | 1.21 | 55.04 | 0.61 |
| V-22 | 63.01 | 0.16 | 23.08 | 1.69 |
| V-23 | 55.78 | 1.09 | 19.21 | 1.55 |
| V-24 | 73.30 | 4.28 | 51.02 | 3.52 |
| V-25 | 53.76 | 1.24 | 24.22 | 0.50 |
| V-26 | 88.37 | 3.61 | 46.41 | 5.32 |
| V-27 | 83.03 | 1.35 | 58.31 | 1.91 |
| V-29 | 63.20 | 0.66 | 41.39 | 1.73 |

(2) The compound to be tested was diluted using DMSO with a four times dilution method to give 10 diluted concentrations, i.e. 500 µM, 125 µM, 31.25 µM, 7.81 µM, 1.95 µM, 0.49 µM, 0.12 µM, 0.03 µM, 7.6 E-03 µM and 1.9 E-03 µM in sequence. Each dilution sample was placed in two wells and the enzyme inhibition IC$_{50}$ of the compound was tested.

TABLE 5

IC$_{50}$ of the compounds for the in vitro inhbition of HDAC1

| Compound | HDAC1 IC$_{50}$ |
|---|---|
| MS-275 | 668 nM |
| V-17 | 735 nM |
| V-18 | 330 nM |
| V-23 | 178 nM |
| V-27 | 212 nM |
| V-29 | 517 nM |

EXAMPLE 51

Determination of the In Vitro Inhibitory Activities of the Compounds Towards Tumor Cells The inhibitory activities of the compounds towards Hut78 T lymphocytic leukemia cells, Jurkat E6-1 human T-cell lymphoma, PANC-1 human pancreatic cancer cells, A549 human lung cancer cells, K562 human chronic myelogenous leukemia cells, Hep3B2.1-7 human liver cancer cells, MDA-MB-435s human breast cancer cells. Colo320 human colorectal cancer cell lines, and PC-3 human prostate cancer at two concentrations of 100 μM and 10 μM were determined. The inhibition percentages were obtained through CCK-8 method. Detailed results are as follows:

TABLE 6

In vitro anti-proliferative effects of the compounds on Hut-78 and PANC-1 cell strains

| Serial number | Compound I.D. | Hut-78 (inhibition %) | | | | PANC-1 (inhibition %) | | | |
|---|---|---|---|---|---|---|---|---|---|
| | | 100 μM | SD 100 μM | 10 μM | SD 10 μM | 100 μM | SD 100 μM | 10 μM | SD 10 μM |
| Positive control | MS-275 | 85.3 | 6.5 | 61.8 | 6.7 | 31.6 | 4.0 | 12.4 | 7.3 |
| 1 | V-1 | 67.2 | 14.6 | 36.0 | 1.9 | 65.4 | 3.8 | 40.2 | 3.1 |
| 2 | V-2 | 82.8 | 2.3 | 63.4 | 4.1 | 74.1 | 2.7 | 20.7 | 9.8 |
| 3 | V-3 | 92.9 | 1.9 | 18.2 | 8.0 | 5.5 | 11.3 | 5.7 | 9.5 |
| 4 | V-4 | 95.8 | 3.0 | 66.4 | 9.6 | 11.9 | 1.7 | 14.4 | 6.8 |
| 5 | V-5 | 43.9 | 2.5 | 15.0 | 6.4 | 45.9 | 2.5 | 10.5 | 14.3 |
| 6 | V-6 | 66.6 | 1.4 | 15.5 | 3.9 | 19.7 | 12.6 | 16.9 | 7.5 |
| 7 | V-7 | 60.3 | 4.8 | 10.7 | 4.8 | 35.2 | 0.0 | 1.1 | 8.4 |
| 8 | V-8 | 83.6 | 1.7 | 17.5 | 6.2 | 34.9 | 6.1 | -1.8 | 3.5 |
| 9 | V-9 | 94.0 | 1.9 | 10.8 | 1.4 | 26.4 | 1.2 | 22.3 | 6.9 |
| 10 | V-10 | 47.5 | 2.1 | 8.1 | 4.0 | 19.0 | 1.5 | 13.0 | 4.7 |
| 11 | V-11 | 84.6 | 3.8 | 28.5 | 1.6 | 21.1 | 6.1 | 24.0 | 3.6 |
| 12 | V-12 | 62.5 | 1.7 | 62.5 | 9.5 | 21.9 | 7.5 | 15.8 | 5.1 |
| 13 | V-13 | 54.0 | 7.6 | 19.8 | 2.0 | 36.8 | 9.1 | 26.0 | 9.2 |
| 14 | V-14 | 91.1 | 2.4 | 22.0 | 5.8 | 15.7 | 5.3 | -2.8 | 9.3 |
| 15 | V-15 | 80.4 | 0.9 | 70.7 | 2.7 | 0.5 | 3.9 | 7.2 | 5.9 |
| 16 | V-16 | 20.7 | 2.1 | 26.2 | 1.2 | 7.8 | 0.8 | 8.0 | 0.5 |
| 17 | V-17 | 93.5 | 4.1 | 73.4 | 1.7 | 25.1 | 10.3 | 12.0 | 8.0 |
| 18 | V-18 | 82.3 | 2.4 | 39.9 | 4.3 | 23.9 | 3.7 | 0.9 | 1.5 |
| 19 | V-19 | 77.0 | 2.7 | 43.0 | 7.0 | 26.2 | 9.0 | 20.2 | 10.9 |
| 20 | V-20 | 85.7 | 4.5 | 44.4 | 3.5 | 52.0 | 1.9 | -1.7 | 5.0 |
| 21 | V-21 | 75.6 | 1.0 | 65.2 | 4.7 | 33.3 | 1.9 | 12.5 | 2.1 |
| 22 | V-22 | 91.8 | 3.9 | 42.3 | 3.9 | 39.4 | 4.2 | 12.3 | 5.8 |
| 23 | V-23 | 93.1 | 2.3 | 59.9 | 3.8 | 4.0 | 2.8 | 9.2 | 4.2 |
| 24 | V-24 | 72.9 | 5.8 | 15.5 | 1.8 | 22.1 | 9.1 | 17.5 | 3.6 |
| 25 | V-25 | 60.0 | 2.1 | 18.1 | 1.8 | 39.5 | 0.5 | 20.8 | 1.4 |
| 26 | V-26 | 86.9 | 1.2 | 79.6 | 2.4 | 40.8 | 6.8 | 5.1 | 9.5 |
| 27 | V-27 | 89.3 | 3.1 | 69.2 | 0.8 | 69.5 | 5.9 | 44.4 | 1.2 |
| 28 | V-29 | 94.0 | 0.3 | 79.4 | 0.8 | 18.4 | 5.3 | 0.9 | 8.9 |
| 29 | V-31 | 95.8 | 4.7 | 28.2 | 2.9 | 50.6 | 0.4 | 20.8 | 1.0 |
| 30 | V-43 | 89.6 | 1.6 | 75.7 | 4.1 | 35.9 | 1.7 | 3.1 | 1.1 |
| 31 | V-46 | 93.4 | 3.1 | 16.4 | 2.8 | 70.4 | 4.1 | 8.1 | 1.0 |
| 32 | V-47 | 88.3 | 2.5 | 9.9 | 2.3 | 43.0 | 3.8 | 2.8 | 3.9 |
| 33 | V-48 | 87.4 | 5.3 | 75.4 | 3.6 | 51.8 | 6.9 | -2.2 | 6.8 |

TABLE 7

In vitro anti-proliferative effects of the compounds on Jurkat E6-1 and K562 cell strains

| Serial number | Compound I.D. | Jurkat E6-1 (inhibition %) | | | | K562 (inhibition %) | | | |
|---|---|---|---|---|---|---|---|---|---|
| | | 100 μM | SD 100 μM | 10 μM | SD 10 μM | 100 μM | SD 100 μM | 10 μM | SD 10 μM |
| Positive control | MS-275 | 96.1 | 0.8 | 89.5 | 1.5 | 74.6 | 2.1 | 66.2 | 1.5 |
| 1 | V-1 | 79.3 | 0.7 | 48.5 | 0.7 | 30.8 | 5.4 | 22.4 | 1.6 |
| 2 | V-2 | 85.9 | 0.3 | 58.5 | 2.1 | 64.4 | 3.7 | 21.0 | 8.0 |
| 3 | V-3 | 96.0 | 0.8 | 27.1 | 2.4 | 85.1 | 1.6 | 51.0 | 4.0 |

TABLE 7-continued

In vitro anti-proliferative effects of the compounds on Jurkat E6-1 and K562 cell strains

| Serial number | Compound I.D. | Jurkat E6-1 (inhibition %) | | | | K562 (inhibition %) | | | |
| --- | --- | --- | --- | --- | --- | --- | --- | --- | --- |
| | | 100 µM | SD 100 µM | 10 µM | SD 10 µM | 100 µM | SD 100 µM | 10 µM | SD 10 µM |
| 4 | V-4 | 23.7 | 6.2 | 5.4 | 5.5 | 38.1 | 6.9 | −1.3 | 6.6 |
| 5 | V-5 | 87.9 | 0.9 | 62.2 | 1.8 | 83.2 | 3.0 | 49.4 | 3.0 |
| 6 | V-6 | 93.3 | 2.0 | 27.2 | 3.5 | 87.2 | 2.0 | 53.6 | 2.1 |
| 7 | V-7 | 91.0 | 0.3 | 26.4 | 3.7 | 82.6 | 1.3 | 29.7 | 3.3 |
| 8 | V-8 | 96.3 | 0.2 | 36.4 | 2.2 | 94.5 | 1.0 | 56.9 | 3.0 |
| 9 | V-9 | 22.8 | 1.2 | 0.9 | 3.2 | 30.3 | 1.8 | −2.8 | 7.2 |
| 10 | V-10 | 72.8 | 4.3 | 25.3 | 7.3 | 62.1 | 1.5 | 45.0 | 2.7 |
| 11 | V-11 | 26.3 | 3.5 | 18.6 | 1.7 | 32.3 | 0.2 | 20.4 | 6.8 |
| 12 | V-12 | 87.4 | 2.3 | 25.0 | 7.9 | 69.8 | 2.8 | 49.3 | 2.2 |
| 13 | V-13 | 77.8 | 2.4 | 19.1 | 2.7 | 65.1 | 0.7 | 25.0 | 1.8 |
| 14 | V-14 | 96.5 | 0.2 | 23.8 | 4.3 | 88.7 | 1.4 | 34.0 | 8.4 |
| 15 | V-15 | 13.9 | 4.2 | 33.7 | 3.2 | 11.9 | 8.6 | 27.2 | 0.8 |
| 16 | V-16 | 22.1 | 3.0 | 37.2 | 6.3 | 29.7 | 2.0 | 42.8 | 2.3 |
| 17 | V-17 | 80.2 | 1.5 | 20.3 | 1.9 | 72.4 | 2.3 | 33.6 | 4.2 |
| 18 | V-18 | 95.7 | 0.2 | 76.6 | 1.8 | 87.5 | 2.5 | 58.5 | 7.1 |
| 19 | V-19 | 80.9 | 2.0 | 58.3 | 2.2 | 85.8 | 1.7 | 54.3 | 2.6 |
| 20 | V-20 | 89.4 | 1.6 | 84.8 | 1.5 | 92.9 | 1.6 | 64.3 | 4.9 |
| 21 | V-21 | 89.7 | 0.4 | 49.3 | 2.9 | 85.2 | 2.0 | 52.2 | 2.5 |
| 22 | V-22 | 88.2 | 1.3 | 83.1 | 1.7 | 83.4 | 3.1 | 60.9 | 4.0 |
| 23 | V-23 | 52.7 | 3.5 | 4.7 | 2.3 | 61.2 | 1.4 | 12.8 | 2.3 |
| 24 | V-24 | 91.4 | 2.3 | 30.7 | 3.7 | 75.3 | 2.8 | −1.7 | 7.3 |
| 25 | V-25 | 83.3 | 2.2 | 12.5 | 0.7 | 64.8 | 4.5 | 34.1 | 3.5 |
| 26 | V-26 | 95.1 | 0.8 | 76.9 | 1.4 | 88.2 | 2.1 | 54.0 | 3.8 |
| 27 | V-27 | 87.6 | 0.7 | 31.6 | 2.1 | 75.0 | 3.5 | 45.0 | 2.6 |
| 28 | V-29 | 96.2 | 1.7 | 51.5 | 3.3 | 83.8 | 1.8 | 57.4 | 3.6 |
| 29 | V-31 | 93.7 | 0.3 | 62.4 | 0.9 | 67.7 | 1.5 | 27.9 | 2.3 |
| 30 | V-43 | 96.8 | 1.0 | 69.1 | 0.9 | 60.8 | 0.3 | 13.8 | 1.6 |
| 31 | V-46 | 1.9 | 1.8 | 14.8 | 3.0 | 18.9 | 10.6 | 27.3 | 6.1 |
| 32 | V-47 | 76.6 | 0.7 | 59.4 | 1.1 | 62.1 | 5.7 | 58.0 | 3.4 |
| 33 | V-48 | 61.9 | 2.9 | 9.7 | 2.9 | 57.2 | 2.3 | 20.0 | 6.6 |

TABLE 8

In vitro anti-proliferative effects of the compounds on A549 and MDA-MB-435s cell strains

| Serial number | Compound I.D. | A549 (inhibition %) | | | | 435s (inhibition %) | | | |
| --- | --- | --- | --- | --- | --- | --- | --- | --- | --- |
| | | 100 µM | SD 100 µM | 10 µM | SD 10 µM | 100 µM | SD 100 µM | 10 µM | SD 10 µM |
| Positive control | MS-275 | 92.3 | 0.3 | 58.9 | 11.2 | 59.3 | 5.3 | 2.7 | 6.0 |
| 1 | V-1 | 89.7 | 0.8 | 50.6 | 0.9 | 87.5 | 3.0 | 26.7 | 5.4 |
| 2 | V-2 | 84.8 | 1.1 | 65.6 | 1.6 | 86.9 | 1.8 | 35.8 | 1.9 |
| 3 | V-3 | 72.3 | 6.4 | −7.8 | 1.2 | 85.5 | 0.8 | 4.5 | 2.6 |
| 4 | V-4 | −19.4 | 38.8 | −43.9 | 50.0 | −10.4 | 4.7 | −20.7 | 7.6 |
| 5 | V-5 | −13.1 | 14.8 | −44.3 | 44.3 | 84.1 | 8.1 | −14.3 | 5.3 |
| 6 | V-6 | 45.7 | 2.8 | −16.9 | 1.9 | 79.1 | 1.8 | 8.0 | 5.1 |
| 7 | V-7 | 24.9 | 14.0 | −7.4 | 13.4 | 85.4 | 9.2 | −16.5 | 2.8 |
| 8 | V-8 | 38.0 | 60.8 | −5.9 | 2.7 | 94.5 | 0.5 | 14.2 | 4.9 |
| 9 | V-9 | 42.3 | 3.2 | 24.6 | 10.8 | 11.8 | 6.0 | −11.9 | 2.8 |
| 10 | V-10 | 40.1 | 0.3 | −4.4 | 0.6 | 82.9 | 1.4 | 9.4 | 10.1 |
| 11 | V-11 | 12.9 | 6.1 | 15.3 | 8.5 | 42.4 | 1.2 | 30.6 | 7.2 |
| 12 | V-12 | 55.1 | 1.5 | −9.0 | 3.7 | 77.2 | 4.5 | 5.7 | 11.5 |
| 13 | V-13 | 57.1 | 10.3 | 18.3 | 3.0 | 89.1 | 2.0 | 27.5 | 2.9 |
| 14 | V-14 | 72.2 | 1.5 | −17.6 | 1.8 | 63.9 | 1.4 | 19.5 | 3.1 |
| 15 | V-15 | 3.5 | 5.0 | 4.7 | 5.0 | 21.0 | 4.1 | 21.6 | 2.1 |
| 16 | V-16 | 65.7 | 0.2 | 48.7 | 10.9 | 50.4 | 3.2 | 49.8 | 2.6 |
| 17 | V-17 | 67.9 | 3.0 | 29.8 | 5.3 | 73.3 | 3.7 | 32.5 | 8.1 |
| 18 | V-18 | 79.1 | 0.5 | 9.5 | 1.5 | 81.4 | 2.5 | 22.7 | 5.6 |

TABLE 8-continued

In vitro anti-proliferative effects of the compounds on A549 and MDA-MB-435s cell strains

| Serial number | Compound I.D. | A549 (inhibition %) | | | | 435s (inhibition %) | | | |
|---|---|---|---|---|---|---|---|---|---|
| | | 100 μM | SD 100 μM | 10 μM | SD 10 μM | 100 μM | SD 100 μM | 10 μM | SD 10 μM |
| 19 | V-19 | 37.3 | 4.1 | 6.3 | 2.9 | 77.0 | 7.7 | 33.0 | 5.5 |
| 20 | V-20 | 41.3 | 3.3 | 0.0 | 5.3 | 57.8 | 4.8 | 17.0 | 7.6 |
| 21 | V-21 | 96.4 | 0.4 | 17.1 | 3.6 | 88.8 | 11.7 | 25.2 | 5.9 |
| 22 | V-22 | 69.9 | 1.3 | 21.8 | 1.6 | 81.4 | 6.6 | 18.0 | 4.6 |
| 23 | V-23 | 6.2 | 6.0 | −7.4 | 11.4 | 42.9 | 6.0 | 21.5 | 4.3 |
| 24 | V-24 | 20.8 | 5.1 | 7.3 | 2.0 | 24.5 | 4.7 | −10.8 | 11.5 |
| 25 | V-25 | 12.0 | 3.9 | 2.4 | 8.0 | 61.2 | 2.2 | 30.8 | 6.5 |
| 26 | V-26 | 63.7 | 1.5 | 4.2 | 5.7 | 73.6 | 5.9 | 16.6 | 3.2 |
| 27 | V-27 | 97.7 | 5.9 | 82.8 | 1.7 | 76.3 | 2.2 | 28.5 | 5.8 |
| 28 | V-29 | 69.8 | 1.2 | 6.3 | 0.9 | 78.5 | 1.7 | 10.1 | 6.3 |
| 29 | V-31 | 88.8 | 1.0 | 56.3 | 0.7 | 89.2 | 1.0 | 24.2 | 6.2 |
| 30 | V-43 | 85.5 | 0.3 | 41.2 | 1.1 | 86.4 | 1.9 | 18.8 | 6.3 |
| 31 | V-46 | 4.1 | 4.6 | 7.7 | 2.2 | 4.1 | 5.8 | 16.4 | 4.1 |
| 32 | V-47 | 8.0 | 0.4 | 9.4 | 2.0 | 29.2 | 3.5 | 21.8 | 5.8 |
| 33 | V-48 | 9.8 | 7.6 | 3.9 | 7.0 | 26.6 | 4.4 | 10.0 | 11.1 |

TABLE 9

In vitro anti-proliferative effects of the compounds or Hep3B and PC-3 cell strains

| Serial number | Compound I.D. | Hep3B (inhibition %) | | | | PC-3 (inhibition %) | | | |
|---|---|---|---|---|---|---|---|---|---|
| | | 100 μM | SD 100 μM | 10 μM | SD 10 μM | 100 μM | SD 100 μM | 10 μM | SD 10 μM |
| Positive control | MS-275 | 52.1 | 0.1 | 10.8 | 7.5 | 71.5 | 0.4 | 12.5 | 3.2 |
| 1 | V-1 | 37.4 | 17.5 | 2.6 | 8.0 | 91.5 | 0.5 | 79.5 | 0.4 |
| 2 | V-2 | 53.6 | 10.4 | 31.2 | 10.4 | 92.4 | 0.8 | 90.3 | 1.2 |
| 3 | V-3 | 59.2 | 3.5 | −12.3 | 6.9 | 36.9 | 2.7 | 0.6 | 8.4 |
| 4 | V-4 | −12.1 | 2.3 | −10.2 | 6.4 | 15.9 | 8.2 | 5.2 | 16.1 |
| 5 | V-5 | 66.6 | 4.2 | 7.3 | 11.3 | 66.7 | 5.8 | 0.0 | 6.6 |
| 6 | V-6 | 57.5 | 10.7 | −7.0 | 24.4 | 56.0 | 12.1 | 23.7 | 4.1 |
| 7 | V-7 | 53.2 | 15.7 | 8.1 | 4.6 | 49.8 | 6.9 | 8.1 | 12.4 |
| 8 | V-8 | 90.4 | 2.6 | 5.0 | 9.9 | 89.3 | 3.2 | 29.7 | 13.2 |
| 9 | V-9 | 26.2 | 7.6 | 27.0 | 11.2 | 19.3 | 5.5 | 5.1 | 8.5 |
| 10 | V-10 | 31.3 | 0.2 | 3.7 | 9.8 | 57.4 | 6.0 | 13.7 | 11.8 |
| 11 | V-11 | 43.0 | 2.5 | 22.3 | 17.7 | 18.8 | 2.1 | 21.9 | 7.5 |
| 12 | V-12 | 67.1 | 10.0 | 4.7 | 26.2 | 61.3 | 7.5 | 25.5 | 22.1 |
| 13 | V-13 | 69.8 | 6.4 | 21.5 | 6.0 | 48.5 | 2.5 | −1.9 | 1.3 |
| 14 | V-14 | 79.3 | 2.3 | 7.2 | 11.1 | 84.4 | 2.5 | 22.9 | 8.5 |
| 15 | V-15 | 11.2 | 11.6 | 16.3 | 7.5 | 8.6 | 4.6 | 10.9 | 4.7 |
| 16 | V-16 | 13.5 | 8.5 | 24.8 | 2.0 | 3.4 | 1.4 | 5.1 | 11.2 |
| 17 | V-17 | 45.7 | 0.4 | 18.4 | 9.3 | 67.1 | 4.7 | 41.8 | 7.1 |
| 18 | V-18 | 75.1 | 2.4 | 13.8 | 5.2 | 72.2 | 3.9 | 45.2 | 1.9 |
| 19 | V-19 | 49.9 | 6.9 | 25.4 | 9.5 | 61.0 | 2.9 | 50.2 | 2.0 |
| 20 | V-20 | 60.0 | 6.3 | 23.5 | 5.2 | 75.5 | 0.5 | 48.1 | 2.6 |
| 21 | V-21 | 68.1 | 4.9 | 11.0 | 9.4 | 64.2 | 2.8 | 40.1 | 3.6 |
| 22 | V-22 | 69.2 | 2.8 | 38.3 | 13.8 | 69.0 | 1.3 | 44.6 | 3.9 |
| 23 | V-23 | 28.1 | 10.0 | 1.0 | 2.8 | 40.2 | 14.0 | 7.0 | 1.7 |
| 24 | V-24 | 69.5 | 0.7 | 14.3 | 8.5 | 63.7 | 2.3 | 13.1 | 2.2 |
| 25 | V-25 | 40.6 | 2.8 | 11.3 | 8.1 | 22.1 | 4.7 | −9.4 | 11.8 |
| 26 | V-26 | 63.5 | 3.0 | 11.7 | 7.2 | 52.6 | 0.2 | 8.7 | 7.0 |
| 27 | V-27 | 68.3 | 0.8 | −12.3 | 5.6 | 59.9 | 3.2 | 43.8 | 5.8 |
| 28 | V-29 | 60.5 | 4.0 | 22.5 | 6.6 | 94.5 | 0.5 | 88.0 | 0.8 |
| 29 | V-31 | 51.7 | 26.7 | −5.0 | 0.4 | 38.8 | 9.1 | 6.3 | 7.8 |
| 30 | V-43 | 58.8 | 1.5 | 21.2 | 3.1 | 89.4 | 0.7 | 81.4 | 0.3 |
| 31 | V-46 | −5.0 | 15.4 | 17.5 | 24.0 | −2.4 | 3.0 | −1.7 | 1.5 |
| 32 | V-47 | 19.2 | 15.2 | 11.2 | 24.7 | 12.8 | 8.6 | 7.2 | 9.4 |
| 33 | V-48 | 20.5 | 12.2 | −14.0 | 9.7 | 14.8 | 7.9 | −16.4 | 7.2 |

TABLE 10

In vitro anti-proliferative effects of the compounds on Colo320 cell strain

| | Compound | Colo320 (inhibition %) | | | |
|---|---|---|---|---|---|
| Serial number | I.D. | 100 μM | SD 100 μM | 10 μM | SD 10 μM |
| Positive control | MS-275 | 61.6 | 0.5 | 18.0 | 4.6 |
| 1 | V-1 | 78.3 | 1.2 | 33.7 | 6.4 |
| 2 | V-2 | 92.9 | 12.4 | 39.6 | 1.1 |
| 3 | V-3 | 47.2 | 3.6 | −7.1 | 5.9 |
| 4 | V-4 | 16.8 | 12.2 | 7.1 | 5.0 |
| 5 | V-5 | 45.3 | 2.1 | 13.0 | 4.4 |
| 6 | V-6 | 59.2 | 4.1 | −5.5 | 4.2 |
| 7 | V-7 | 48.5 | 3.2 | 8.9 | 5.4 |
| 8 | V-8 | 86.4 | 0.2 | −1.8 | 2.8 |
| 9 | V-9 | 4.2 | 6.6 | 4.4 | 4.0 |
| 10 | V-10 | 23.3 | 6.0 | 6.4 | 6.3 |
| 11 | V-11 | 4.1 | 4.6 | 2.6 | 4.2 |
| 12 | V-12 | 46.1 | 2.7 | 2.4 | 3.7 |
| 13 | V-13 | 34.3 | 4.1 | 0.9 | 4.0 |
| 14 | V-14 | 82.7 | 18.7 | −14.3 | 4.8 |
| 15 | V-15 | 3.9 | 2.5 | 15.3 | 5.4 |
| 16 | V-16 | −17.1 | 3.2 | −2.3 | 7.9 |
| 17 | V-17 | 28.9 | 4.0 | 4.9 | 7.9 |
| 18 | V-18 | 56.3 | 14.5 | 7.7 | 4.0 |
| 19 | V-19 | 40.1 | 4.6 | 12.9 | 6.1 |
| 20 | V-20 | 58.8 | 19.4 | 6.5 | 2.7 |
| 21 | V-21 | 45.9 | 3.6 | 9.5 | 7.8 |
| 22 | V-22 | 40.8 | 15.8 | 5.4 | 3.8 |
| 23 | V-23 | 5.9 | 4.6 | 7.3 | 7.5 |
| 24 | V-24 | 16.5 | 8.6 | −1.7 | 5.1 |
| 25 | V-25 | 14.1 | 1.0 | 7.9 | 4.2 |
| 26 | V-26 | 44.4 | 11.2 | −0.2 | 6.0 |
| 27 | V-27 | 82.3 | 3.9 | 60.0 | 3.9 |
| 28 | V-29 | 35.5 | 4.1 | −7.2 | 1.0 |
| 29 | V-31 | 77.0 | 2.8 | 76.3 | 20.9 |
| 30 | V-43 | 59.4 | 2.0 | 19.1 | 2.4 |
| 31 | V-46 | −9.0 | 7.5 | 13.7 | 3.8 |
| 32 | V-47 | 6.0 | 2.8 | 11.0 | 4.6 |
| 33 | V-48 | 17.9 | 1.6 | 2.9 | 4.1 |

TABLE 11

Determination of the $IC_{50}$ values for the in vitro anti-proliferative effects of the compounds on tumor cell strains

| | $IC_{50}$ (μM) | | | | | | |
|---|---|---|---|---|---|---|---|
| Compound | PC-3 | A549 | Colo320 | Hep3B | Hut78 | K562 | Jurkat E6-1 |
| MS-275 | 0.5020 | 2.278 | 0.5222 | 6.816 | 0.5281 | 4.663 | 0.5614 |
| V-9 | 12.17 | 29.92 | 88.405 | 52.172 | 0.2311 | 19.851 | 12.353 |
| V-14 | 3.568 | 5.089 | 26.997 | 15.997 | 0.0558 | 2.811 | 1.392 |
| V-27 | | 3.136 | | 1.523 | 0.3557 | 0.4369 | 0.4578 |

EXAMPLE 52

Test of Maximum Tolerance Dose as a Measure of the Compounds' Toxicity Through Intragastrical Administration Forty ICR mice, half female and half male, weighing 8~20 g were divided into four groups, 10 mice in each group. After the mice were fasted for 6 h, the compound to be tested was administrated intragastrically to each group at a volume of 0.3 ml/10 g by using a sterile plastic syringe. General physical signs and the deaths of the animals were record at 1, 2 and 4 h after the administration. The animals were then observed continuously for 14 days and their weights, physical signs and deaths were observed and recorded every day. Dead animals were dissected to see if there was any visible pathological change in the animal's viscera and pathological examination was performed on suspicious tissues and organs. A part of the experimental results is as follows.

The maximum tolerance doses of Compounds V-1, V-4, V-6, V-9, V-13, V-17, V-20, V-25, V-29, V-43, and V-47 when administrated intragastrically are over 5000 mg/kg in mice, and the same of Compounds V-2, V-5, V-11, V-14, V-18, V-22, V-24, V-27 and V-46 are over 2000 mg/kg.

EXAMPLE 53

TABLE 12

Effects of the compounds on hERG potassium channel

| Compound | Half inhibition concentration for the effect on hERG potassium current, $IC_{50}$ (μM) | Maximum inhibition percentage at 10 μM (%) |
|---|---|---|
| V-9 | >10 | 21.5 ± 0.4 |
| V-27 | >10 | 29.9 ± 6.7 |

EXAMPLE 54

TABLE 13

Preliminary pharmacokinetic results of the compounds

| Compound | Intravenous half-life in hours (rat, 2 mg/kg, i.v.) | Oral half-life in hours | Oral bioavailability % |
|---|---|---|---|
| V-9 | 1.27 | 4.53 | 18.99 |
| V-27 | 0.95 | 3.37 | 28.6 |

EXAMPLE 55

In Vivo Test of Compounds for Human Tumors Transplanted in Nude Mice

The inhibitory effect of Compound V-9 (50 mg/kg) on the growth of human PC-3 tumors transplanted in nude mice was investigated in vivo using MS-275 as the positive control. The inhibitory effect of Compound V-27 (50 mg/kg) on the growth of human A549 tumors transplanted in nude mice was investigated in vivo using MS-275 as the positive control. The experimental results are as follows.

TABLE 14

In vivo test of compounds for human tumors transplanted in nude mice

| Compound | In vivo test for human tumors transplanted in nude mice (50 mg/kg) inhibition % (8 mice in each group) | |
|---|---|---|
| | PC-3 (human prostate cancer) | A549 (lung cancer) |
| MS-275 | 89.60% (4 deaths) | 79.41% (3 deaths) |
| V-9 | 36.97% (no death) | |
| V-27 | | 61.83% (no death) |

EXAMPLE 56

Tablet

| | |
|---|---|
| The compound of any one of Examples 1-48 | 10 mg |
| Sucrose | 150 mg |
| Corn starch | 38 mg |
| Calcium stearate | 2 mg |

Preparation method: The active ingredient, sucrose and corn starch can be mixed, wetted by adding water and stirred thoroughly to obtain a homogenous mixture which can be dried, grounded and sieved. Then calcium stearate can be added and mixed homogenously before pressing to form a tablet. Each tablet weighs 200 mg, containing 10 mg active ingredient.

EXAMPLE 57

Injection

| | |
|---|---|
| The compound of any one of Examples 1-48 | 20 mg |
| Water for injection | 80 mg |

Preparation method: The active ingredient can be dissolved in water for injection, mixed homogenously and filtered. The resultant solution can be dispensed into ampoules under aseptic conditions, 10 mg in each ampoule with 2 mg active ingredient therein.

The invention claimed is:
1. A compound selected from the group consisting of:
V-1 N-(2-aminophenyl)-4-(quinazoline-4-amino)benzamide,
V-2 N-(2-amino-4-pyridyl)-4-(quinazoline-4-amino)benzamide,
V-3 N-(2-amino-5-fluorophenyl)-4-(quinazoline-4-amino)benzamide,
V-4 N-(2-amino-4-pyridyl)-4-(6,7-dimethoxyquinazoline-4-amino)benzamide,
V-5 N-(2-aminophenyl)-4-(6-methoxyquinazoline-4-amino)benzamide,
V-6 N-(2-amino-5-fluorophenyl)-4-(6-methoxyquinazoline-4-amino)benzamide,
V-7 N-(2-aminophenyl) 4-(5-methoxyquinazoline-4-amino)benzamide,
V-8 N-(2-amino-4-pyridyl)-4-(5-methoxyquinazoline-4-amino)benzamide,
V-9 N-(2-aminophenyl)-4-(8-methoxyquinazoline-4-amino)benzamide,
V-10 N-(2-amino-5-fluorophenyl)-4-(8-methoxyquinazoline-4-amino)benzamide,
V-11 N-(2-aminophenyl)-4-(6-nitroquinazoline-4-amino)benzamide,
V-12 N-(2-aminophenyl)-4-(6-fluoroquinazoline-4-amino)benzamide,
V-13 N-(2-aminophenyl)-4-(7-fluoroquinazoline-4-amino)benzamide,
V-14 N-(2-amino-5-fluorophenyl)-4-(8-fluoroquinazoline-4-amino)benzamide,
V-15 N-(2-aminophenyl)-4-(6,7-dimethoxyethoxyquinazoline-4-amino)benzamide,
V-16 N-(2-amino-4-pyridyl)-4-(6,7-dimethoxyethoxyquinazoline-4-amino)benzamide,
V-17 N-(2-aminophenyl)-4-[7-methoxy-6-(3-morpholinylpropoxy)quinazoline-4-amino]benzamide,
V-18 N-(2-amino-5-fluorophenyl)-4-[7-methoxy-6-(3-morpholinylpropoxy)quinazoline-4-amino]benzamide,
V-19 N-(2-aminophenyl)-4-[6-(5-((2-(methylsulfonyl)ethylamino)methyl)furyl)quinazoline-4-amino]benzamide,
V-20 N-(2-amino-5-fluorophenyl)-4-[6-(5-((2-(methylsulfonyl)ethylamino)methyl)furyl)quinazoline-4-amino]benzamide,
V-21 N-(2-aminophenyl)-4-(6-acetamidoquinazoline-4-amino)benzamide,
V-22 N-(2-aminophenyl)-4-(6-methoxycarbonylmethylquinazoline-4-amino)benzamide,
V-23 N-[2-amino-5-(2-thienyl)phenyl]-4-(6,7-dimethoxyquinazoline-4-amino)benzamide,
V-24 N-[2-amino-5-(phenyl)phenyl]-4-(6,7-dimethoxyquinazoline-4-amino)benzamide,
V-25 N-[2-amino-5-(2-furyl)phenyl]-4-(6,7-dimethoxyquinazoline-4-amino)benzamide,
V-26 N-(2-amino-4-pyridyl)-4-[(quinazoline-4-amino)methyl]benzamide,
V-27 N-(2-aminophenyl)-4-[(quinazoline-4-amino)methyl]benzamide,
V-28 N-[2-amino-5-(2-thienyl)phenyl]-4-[(quinazoline-4-amino)methyl]benzamide,
V-29 N-(2-amino-5-fluorophenyl)-4-[(quinazoline-4-amino)methyl]benzamide,
V-30 N-(2-amino-4-pyridyl)-4-[(6,7-dimethoxyquinazoline-4-amino)methyl]benzamide,
V-31 N-[2-amino-5-(2-thienyl)phenyl]-4-[(6,7-dimethoxyquinazoline-4-amino)methyl]benzamide,
V-32 N-(2-aminophenyl)-4-[(7-methoxyquinazoline-4-amino)methyl]benzamide,
V-33 N-(2-aminophenyl)-4-[(6-methoxyquinazoline-4-amino)methyl]benzamide,
V-34 N-(2-aminophenyl)-4-[(8-methoxyquinazoline-4-amino)methyl]benzamide,
V-35 N-(2-amino-5-fluorophenyl)-4-[(8-methoxyquinazoline-4-amino)methyl]benzamide,
V-36 N-(2-amino-5-(phenyl)phenyl)-4-[(8-methoxyquinazoline-4-amino)methyl]benzamide,
V-37 N-(2-aminophenyl)-4-[(6-nitroquinazoline-4-amino)methyl]benzamide,
V-38 N-(2-aminophenyl)-4-[(6,7-dimethoxyethoxyquinazoline-4-amino)methyl]benzamide,
V-39 N-(2-amino-4-pyridyl)-4-[(6,7-dimethoxyethoxyquinazoline-4-amino)methyl]benzamide,
V-40 N-(2-amino-5-fluorophenyl)-4-[(6,7-dimethoxyethoxyquinazoline-4-amino)methyl]benzamide,
V-41 N-(2-aminophenyl)-4-[(7-methoxy-6-(3-morpholinylpropoxy)quinazoline-4-amino)methyl]benzamide,

V-42 N-(2-amino-4-pyridyl)-4-[(7-methoxy-6-(3-morpholinylpropoxy)quinazoline-4-amino)methyl]benzamide, V-43 N-(2-aminophenyl)-4-[(8-fluoroquinazoline-4-amino)methyl]benzamide, V-44 N-(2-amino-4-pyridyl)-4-[(8-fluoroquinazoline-4-amino)methyl]benzamide, V-45 N-(2-amino-5-(2-furyl)phenyl)-4-[(8-fluoroquinazoline-4-amino)methyl]benzamide, V-46 N-(2-aminophenyl)-4-[(6-acetamidoquinazoline-4-amino)methyl]benzamide, V-47 N-(2-amino-4-pyridyl)-4-[(6-acetamidoquinazoline-4-amino)methyl]benzamide, or V-48 N-[2-amino-5-(2-furyl)phenyl]-4-[(6-acetamidoquinazoline-4-amino)methyl]benzamide.

2. A pharmaceutical composition comprising a therapeutically effective amount of the compound of claim 1 or a salt thereof, and a pharmaceutically acceptable carrier.

* * * * *